(12) United States Patent
Fujii

(10) Patent No.: US 10,036,883 B2
(45) Date of Patent: Jul. 31, 2018

(54) ENDOSCOPE MAGNIFICATION OPTICAL SYSTEM AND ENDOSCOPE

(71) Applicant: HOYA CORPORATION, Tokyo (JP)

(72) Inventor: Hiroaki Fujii, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 15/513,327

(22) PCT Filed: Aug. 29, 2016

(86) PCT No.: PCT/JP2016/075158
§ 371 (c)(1),
(2) Date: Mar. 22, 2017

(87) PCT Pub. No.: WO2017/043352
PCT Pub. Date: Mar. 16, 2017

(65) Prior Publication Data
US 2018/0003944 A1 Jan. 4, 2018

(30) Foreign Application Priority Data
Sep. 7, 2015 (JP) .................................. 2015-176174

(51) Int. Cl.
*G02B 23/24* (2006.01)
*G02B 15/15* (2006.01)
(Continued)

(52) U.S. Cl.
CPC ...... *G02B 23/2438* (2013.01); *A61B 1/00188* (2013.01); *G02B 15/15* (2013.01);
(Continued)

(58) Field of Classification Search
CPC .. G02B 23/24; G02B 23/243; G02B 23/2415; G02B 23/2438; G02B 15/14;
(Continued)

(56) References Cited

U.S. PATENT DOCUMENTS 4,493,537 A * 1/1985 Nakahashi ............. G02B 13/04
359/740
5,587,839 A * 12/1996 Miyano .................... G02B 9/34
359/660

(Continued)

FOREIGN PATENT DOCUMENTS

JP    2-136811    5/1990
JP    2004-334070    11/2004
(Continued)

OTHER PUBLICATIONS

International Search Report, along with English-language translation thereof, issued in PCT/JP2016/075158 dated Sep. 27, 2016.

*Primary Examiner* — Loha Ben
(74) *Attorney, Agent, or Firm* — Greenblum & Bernstein, P.L.C.

(57) ABSTRACT

An endoscope magnification optical system includes, in order starting from an object side, a first lens group having positive power, a second lens group having positive power, and a third lens group including at least a meniscus lens with a concave surface facing the object side and a positive lens, and the endoscope magnification optical system is configured to magnify an optical image by moving at least the second lens group in an optical axis direction with respect to the first lens group, which is a fixed lens group, while a distance from a lens surface located the closest to the object of the first lens group to an image plane is kept constant.

9 Claims, 15 Drawing Sheets

(51) Int. Cl.
*A61B 1/00* (2006.01)
*G02B 15/167* (2006.01)
*G02B 15/14* (2006.01)
*G02B 13/02* (2006.01)
*G02B 13/18* (2006.01)

(52) U.S. Cl.
CPC ......... *G02B 23/24* (2013.01); *G02B 23/2415* (2013.01); *A61B 1/00* (2013.01); *G02B 13/02* (2013.01); *G02B 13/18* (2013.01); *G02B 15/14* (2013.01); *G02B 15/167* (2013.01); *G02B 23/243* (2013.01)

(58) Field of Classification Search
CPC .... G02B 15/15; G02B 15/167; G02B 15/177; G02B 15/22; G02B 13/004; G02B 13/009; G02B 13/02; G02B 13/04; G02B 13/12; G02B 13/18; G02B 9/00; G02B 9/34; G02B 9/58; G02B 3/02; A61B 1/00096; A61B 1/00131; A61B 1/00133; A61B 1/00188; A61B 1/0019; A61B 1/00; A61B 1/005
USPC ....... 359/644, 672, 676, 679, 680, 682, 683, 359/694, 695, 715, 716, 745, 747, 753, 359/781, 783
See application file for complete search history.

(56) References Cited

U.S. PATENT DOCUMENTS

| | | | | |
|---|---|---|---|---|
| 5,777,797 A * | 7/1998 | Miyano | ............... | G02B 23/243 359/660 |
| 7,486,449 B2 * | 2/2009 | Miyano | ............... | G02B 23/243 359/770 |
| 8,098,441 B2 * | 1/2012 | Sasamoto | .......... | G02B 23/2407 359/656 |
| 8,130,454 B2 * | 3/2012 | Noguchi | ............ | G02B 23/2438 359/656 |
| 8,203,798 B2 * | 6/2012 | Takato | ............... | A61B 1/00188 359/753 |
| 8,300,325 B2 * | 10/2012 | Katahira | .................. | G02B 9/34 359/752 |
| 8,449,127 B2 * | 5/2013 | Katahira | ............ | A61B 1/00096 128/898 |
| 8,456,767 B2 * | 6/2013 | Takato | ................. | G02B 23/243 359/753 |
| 8,767,320 B2 * | 7/2014 | Fujii | .................. | G02B 23/2438 359/660 |
| 2003/0189768 A1 | 10/2003 | Murayama | | |
| 2004/0246362 A1 | 12/2004 | Konno | | |
| 2005/0141100 A1 | 6/2005 | Kojima et al. | | |
| 2015/0042773 A1 | 2/2015 | Uzawa et al. | | |
| 2016/0154230 A1 | 6/2016 | Katakura | | |
| 2017/0303774 A1 * | 10/2017 | Nasu | .................. | A61B 1/00188 |
| 2018/0017779 A1 * | 1/2018 | Nasu | .................. | G02B 23/2438 |

FOREIGN PATENT DOCUMENTS

| | | |
|---|---|---|
| JP | 2005-189284 | 7/2005 |
| JP | 2005-189638 | 7/2005 |
| JP | 3845331 | 11/2006 |
| JP | 4426236 | 3/2010 |
| JP | 2012-47909 | 3/2012 |
| WO | 2014/129089 | 8/2014 |
| WO | 2015/025843 | 2/2015 |

* cited by examiner

ENDOSCOPE MAGNIFICATION OPTICAL SYSTEM AND ENDOSCOPE

TECHNICAL FIELD

The present invention relates to an endoscope magnification optical system and an endoscope in which an endoscope magnification optical system is incorporated.

In the field of medicine, endoscopes (fiberscopes or electronic scopes) are commonly known as devices for observing the interior of a body cavity of a patient, and are provided for practical use. In order to observe abnormalities in detail, some of these types of endoscopes are equipped with a magnification optical system having a magnification function.

For example, Japanese Patent 3845331 (hereinafter written as "Patent Document 1") discloses a specific configuration of an endoscope magnification optical system. The endoscope magnification optical system disclosed in Patent Document 1 includes, in order starting from an object side, a first lens group having negative power, a second lens group having positive power, a third 3 lens group having positive power, and a fourth lens group having negative power, and is configured to be able to change the focal length of the entire system while maintaining a focused state by causing the second and third lens groups to move while changing the object distance without changing the entire length from the first lens group to the image plane.

SUMMARY OF INVENTION

Thus, since the endoscope magnification optical system according to Patent Document 1 is configured to move the second and third lens groups having positive power, the amount of freedom in design relating to magnification control is high. However, with this configuration, aberrations are not sufficiently corrected, and in particular, an axial chromatic aberration and a chromatic aberration of magnification change dramatically during magnification. The more changes occur toward the telephoto end, the more the axial chromatic aberration and chromatic aberration of magnification are overcorrected and the more the optical performance deteriorates.

In recent years, high-pixel image sensors have often been mounted in electronic scopes. However, a problem has been indicated in that a high-quality image cannot be obtained even with a high-pixel image sensor if a large aberration occurs in the endoscope magnification optical system.

The present invention has been achieved in view of the foregoing circumstances and it is an object thereof to provide an endoscope magnification optical system according to which aberrations are favorably corrected, and an endoscope in which the endoscope magnification optical system is mounted.

An endoscope magnification optical system according to an embodiment of the present invention includes, in order starting from an object side, a first lens group having negative power, a second lens group having positive power, and a third lens group including at least a meniscus lens with a concave surface facing the object side and a positive lens, the endoscope magnification optical system being configured to magnify an optical image by moving at least the second lens group in an optical axis direction with respect to the first lens group, which is a fixed lens group, while a distance from a lens surface located the closest to the object of the first lens group to an image plane is kept constant.

Also, the endoscope magnification optical system according to an embodiment of the present invention may be configured such that in a case where a magnification of the second lens group at a telephoto end is defined as $m_{2t}$, a magnification of the second lens group at a wide angle end is defined as $m_{2w}$, a movement amount of the second lens group that is needed to change from the telephoto end to the wide angle end or from the wide angle end to the telephoto end is defined as d (unit: mm), and a focal length of the second lens group is defined as $f_2$ (unit: mm), the following two conditional expressions:

$$-1 < m_{2t} < m_{2w} < -0.35$$

$$0.3 < d/f_2 < 0.6$$

are satisfied.

Also, in an embodiment of the present invention, it is possible to use a configuration in which the first lens group includes at least one single lens and one doublet.

Also, in an embodiment of the present invention, it is possible to use a configuration in which the first lens group includes at least a negative lens and a doublet, or a doublet having negative power and a meniscus lens with a concave surface facing the object side.

Also, in an embodiment of the present invention, it is possible to use a configuration in which the second lens group is composed of, in order starting from the object side, a positive lens and a doublet having positive power, and in a case where a focal length of the positive lens in the second lens group is defined as $f_{21}$ (unit: mm) and a composite focal length from the first to third lens groups at the wide angle end is defined as $f_w$ (unit: mm), the following conditional expression:

$$2 \leq f_{21}/f_w < 6$$

is satisfied.

Also, in an embodiment of the present invention, it is possible to use a configuration in which the second lens group is composed of, in order starting from the object side, a positive lens, a positive lens, and a doublet having positive power.

In this case, it is possible to use a configuration in which the two positive lenses included in the second lens group have mutually different focal lengths, and in a case where a composite focal length of the two positive lenses is defined as $f_c$ (unit: mm) and a longer focal length of the focal lengths of the two positive lenses is defined as $f_p$ (unit: mm), the following conditional expression:

$$0.3 < f_c/f_p$$

is satisfied.

Also, the endoscope magnification optical system according to an embodiment of the present invention may have a configuration in which an aperture configured to move integrally with the second lens group on the optical axis is included between the first and the second lens groups.

Also, an endoscope according to an embodiment of the present invention is a device in which the above-described endoscope magnification optical system is mounted on a leading end thereof.

According to an embodiment of the present invention, an endoscope magnification optical system according to which aberrations are favorably corrected and an endoscope in which the endoscope magnification optical system is mounted are provided.

DESCRIPTION OF EMBODIMENTS

Hereinafter, an endoscope magnification optical system according to an embodiment of the present invention and an electronic scope including an endoscope magnification optical system will be described with reference to the drawings.

Figure 1:
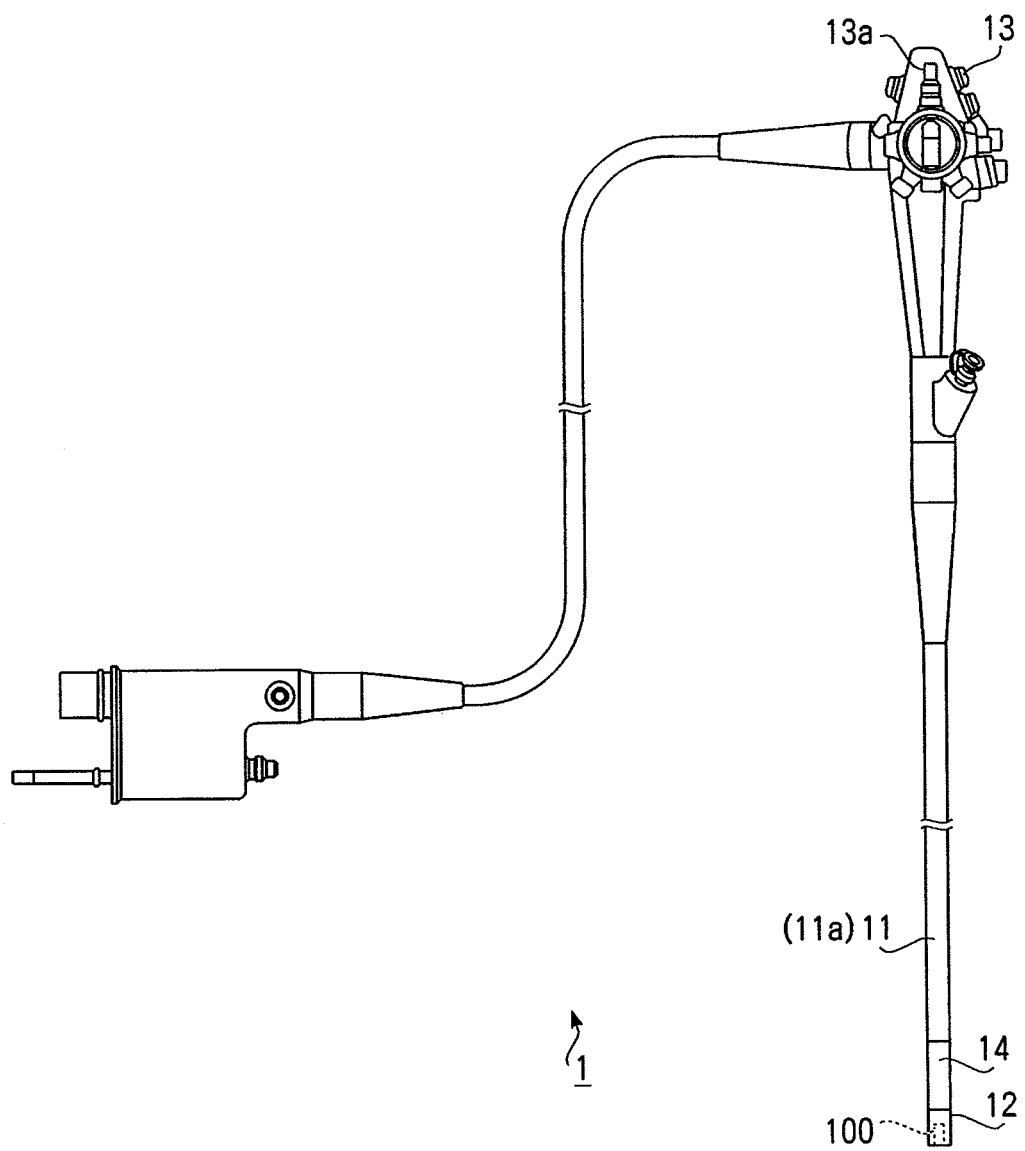
FIG. 1 is an external view showing an exterior of an electronic scope according to an embodiment of the present invention.

FIG. 1 is an external view showing an exterior of an electronic scope 1 according to an embodiment of the present invention. As shown in FIG. 1, the electronic scope 1 includes an insertion portion flexible tube 11 that is covered by a flexible sheath 11a. A leading end portion (bending portion 14) of the insertion portion flexible tube 11 bends in response to a remote operation (specifically, an operation of rotating a bending operation knob 13a) from a hand operation portion 13 coupled to a base end of the insertion portion flexible tube 11. The bending mechanism is a known mechanism incorporated in a common endoscope, and the bending mechanism causes the bending portion 14 to bend by pulling an operation wire linked to the rotation operation of the bending operation knob 13a. A base end of a leading end portion 12 covered by a housing made of hard resin is coupled to the leading end of the bending portion 14. The direction of the leading end portion 12 changes according to the bending operation performed through the rotation operation of the bending operation knob 13a, and thus a region imaged by the electronic scope 1 moves.

An endoscope magnification optical system 100 (the block indicated by diagonal lines in FIG. 1) is incorporated in the interior of the housing made of resin of the leading end portion 12. The endoscope magnification optical system 100 allows light from an object in the imaging region to form an image on a light receiving plane of a solid image sensor (not shown) in order to obtain image data of the object. Examples of the solid image sensor include a CCD (Charge Coupled Device) image sensor or a CMOS (Complementary Metal Oxide Semiconductor) image sensor.

Next, endoscope magnification optical systems 100 according to Working Examples 1 to 7 of the present invention will be described.

Working Example 1

FIGS. 2(a) and 2(b) are cross-sectional views showing an arrangement of the endoscope magnification optical system 100 according to Working Example 1 of the present invention and optical components arranged downstream thereof. FIG. 2(a) is a cross-sectional view showing a lens arrangement when a magnification position is at a wide angle end. FIG. 2(b) is a cross-sectional view showing a lens arrangement when a magnification position is at a telephoto end.

Figure 2:
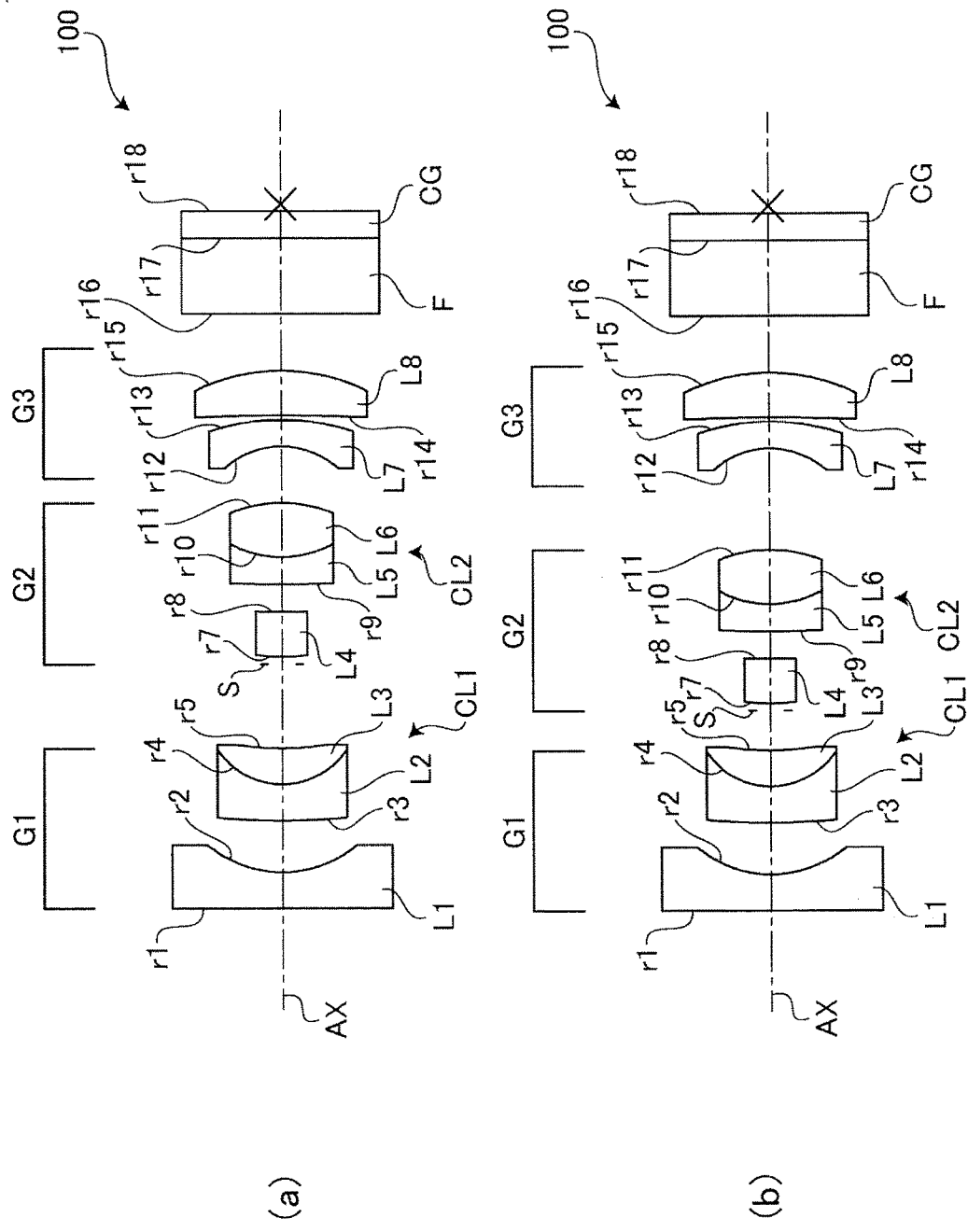
FIG. 2 is a lens arrangement diagram showing a configuration of an endoscope magnification optical system according to Working Example 1 of the present invention.

As shown in FIG. 2, the endoscope magnification optical system 100 according to Working Example 1 has, in order starting from an object (subject) side, a first lens group G1, an aperture S, a second lens group G2, and a third lens group G3. The endoscope magnification optical system 100 according to Working Example 1 is configured to move the second lens group G2 in an optical axis direction AX with respect to the first lens group G1 and the third lens group G3, which are fixed lens groups, while a distance from the lens surface located the closest to the object side of the first lens group to the imaging plane (i.e., the entire length of the endoscope magnification optical system 100) is kept constant, and thus change a focal length of the entire system (composite focal length from the first lens group G1 to the third lens group) while maintaining a focused state, so as to magnify an optical image. The optical lenses constituting the lens groups G1 to G3 have shapes with rotational symmetry centered on the optical axis AX of the endoscope magnification optical system 100. A color correction filter F for a solid image sensor is arranged downstream of the third lens group G3. The color correction filter F is adhered to a cover glass CG that protects the solid image sensor.

The first lens group G1 is a lens group that has negative power and is arranged on the object side relative to the aperture S. The first lens group G1 includes at least, in order starting from the object side, a negative lens L1, and a doublet CL1 obtained by bonding a negative lens L2 and a positive lens L3. The expression "includes at least" is used because a configuration example in which another optical element such as a parallel plate is additionally arranged is also possible in the scope of the technical idea of the present invention. For similar reasons, the expression "includes at least" is used in the description of the second lens group G2 and the third lens group G3 as well.

In other words, the first lens group G1 includes one single lens and one doublet.

Due to the first lens group G1 including one single lens and one doublet (in Working Example 1, one negative lens and one doublet having positive or negative power), a comatic aberration and a chromatic aberration are favorably corrected in the group by dispersing negative power in the first lens group G1 and having positive power. Accordingly, variations in aberrations in the entire system are suppressed, and aberrations are favorably suppressed at every magnification from the wide angle end to the telephoto end.

The second lens group G2 is a lens group that has positive power. The second lens group G2 includes at least, in order starting from the object side, a positive lens L4, and a doublet CL2 that has positive power and is obtained by bonding a negative lens L5 and a positive lens L6. The second lens group G2 moves integrally with the aperture S in the optical axis AX direction in order to magnify the optical image formed on the image receiving plane of the solid image sensor. By integrally moving the second lens group G2 and the aperture S, the occurrence of astigmatism when at the telephoto end is effectively suppressed.

The aperture S is a plate-shaped member having a predetermined circular opening centered on the optical axis AX, or is a light-blocking film that coats the lens surface located the closest to the aperture S of the second lens group G2 (in the configuration example shown in FIG. 2, surface r7 on the object side of the positive lens L4), excluding a predetermined circular region centered on the optical axis AX. The thickness of the aperture S is very thin compared to the thicknesses of the optical lenses constituting the endoscope magnification optical system 100, and can be ignored when calculating the optical performance of the endoscope magnification optical system 100. For this reason, in the present specification, the thickness of the aperture S is considered to be zero in the following description.

The third lens group G3 includes at least, in order starting from the object side, a meniscus lens L7 with a concave surface facing the object side, and a positive lens L8. The meniscus lens L7 having a concave surface facing the object side is arranged on the image side relative to the second lens group G2, or in other words, in the third lens group G3, and it is thereby possible to cause the third lens group G3 to contribute significantly to the magnification required when observing the interior of a body cavity using the electronic scope 1. For this reason, the first lens group G1 and the second lens group G2 can be made smaller, which is advantageous for designing an electronic scope 1 with a smaller diameter. In addition, by arranging the positive lens L8 on the image side with respect to the meniscus lens L7, axial chromatic aberrations and chromatic aberrations of magnification that occur significantly with the meniscus lens L7 can be favorably corrected. Accordingly, aberrations are favorably suppressed at every magnification from the wide angle end to the telephoto end.

In the case where the magnification of the second lens group G2 at the telephoto end is defined as $m_{2t}$, the magnification of the second lens group G2 at the wide angle end is defined as $m_{2w}$, the movement amount of the second lens group G2 that is needed in order to change from the telephoto end to the wide angle end or from the wide angle end to the telephoto end is defined as d (unit: mm), and the focal length of the second lens group G2 is $f_2$ (unit: mm), the endoscope magnification optical system 100 according to Working Example 1 has a configuration in which the following two conditional expressions (1) and (2):

$$-1 < m_{2t} < m_{2w} < -0.35 \quad (1)$$

$$0.3 < d/f_2 < 0.6 \quad (2)$$

are satisfied.

Due to conditional expressions (1) and (2) being satisfied, the endoscope magnification optical system 100 can be designed with a smaller size while having a configuration that is suitable for precise focus adjustment.

If the magnification $m_{2w}$ is greater than or equal to the value on the right side of conditional expression (1), the movement amount of the second lens group G2 that is needed for magnification will increase and the entire length of the endoscope magnification optical system 100 will increase due to the fact that the magnification $m_{2w}$ of the second lens group G2 at the wide angle end is low. For this reason, the entire length of the leading end portion 12 of the electronic scope 1, which is a hard portion, will need to be increased since it is necessary to accommodate the endoscope magnification optical system 100, which has a large length overall, therein. Also, if the magnification mew is greater than or equal to the value on the right side of the conditional expression (1), the change in the optimal object distance when moving the second lens group G2 will increase due to the fact that the magnification $m_{2w}$ of the second lens group G2 on the telephoto end will be relatively large. For this reason, precise focus adjustment will no longer be possible.

If consideration is given to the user-friendliness of the electronic scope 1 when observing the interior of a body cavity, the optimal object distance preferably shortens as the telephoto end is approached from the wide angle end, and preferably reaches its minimum when the telephoto end is reached. However, if the magnification $m_{2t}$ is less than or equal to the value on the left side of conditional expression (1), the optimal object distance will reach its minimum before the telephoto end is reached. For this reason, the user-friendliness of the electronic scope 1 when observing the interior of a body cavity deteriorates.

If the value in the center of conditional expression (2) is greater than or equal to the value on the right side, the magnification ratio between the wide angle end and the telephoto end will be excessively large due to the fact that the power of the second lens group G2 will be excessively high or the movement amount d will be excessively large. Accordingly, the effective F number (on the telephoto end side) during enlarged observation will increase, light amount deficiency and resolution decrease will occur, and for example, the depth of field will decrease, making it difficult to perform observation.

If the value in the center of conditional expression (2) is less than or equal to the value on the left side, focus adjustment will need to be performed with a small movement of the second lens group G2 due to the fact that the power of the second lens group G2 will be excessively weak or the movement amount d will be too small. For this reason, a high-precision focus adjustment mechanism will be needed, which increases the cost and the size of the electronic scope 1. Also, since the focus adjustment range will be excessively small, the user-friendliness of the electronic scope 1 at the time of observing the interior of a body cavity will deteriorate.

Also, in the case where the focal length of the positive lens in the second lens group G2 is defined as $f_{21}$ (unit: mm) and the focal length of the entire system at the wide angle end is defined as $f_w$ (unit: mm), the endoscope magnification optical system 100 according to Working Example 1 has a configuration in which the following conditional expression (3)

$$2 < f_{21}/f_w < 6 \quad (3)$$

is satisfied.

Due to conditional expression (3) being satisfied, an eccentric sensitivity (e.g., an amount of change in aberrations when eccentricity occurs in the arrangement plane or shape surface with respect to the optical axis AX) of the lenses in the second lens group G2 is reduced.

If the value in the center of conditional expression (3) is greater than or equal to the value on the right side, the power of the doublet in the second lens group G2 will be excessively strong, and the eccentric sensitivity of the doublet will increase. Here, in particular, a large astigmatism and chromatic aberration of magnification will occur due to eccentricity in the doublet. Also, the movement amount of the second lens group G2 during magnification will increase, which is not advantageous for designing a smaller endoscope magnification optical system 100.

If the value in the center of conditional expression (3) is less than or equal to the value on the left side, the power of the positive lens in the second lens group G2 will be excessively strong, and the eccentric sensitivity of the positive lens will increase. Here, in particular, a large astigmatism will occur due to eccentricity in the positive lens. Also, a spherical aberration will increase in size as the telephoto end is approached, whereby the resolution will decrease.

Table 1 shows specific numerical value configurations (design values) of the endoscope magnification optical system 100 (and optical components arranged downstream thereof) according to Working Example 1. The upper left field of Table 1 shows values (surface data) at the wide angle end, and the upper right field of Table 1 shows values (surface data) at the telephoto end. Surface numbers NO shown in Table 1 are numbers that sequentially denote surfaces (including aperture S) that are aligned from the object side to the image side in FIG. 2. In Table 1, R (unit: mm) indicates the curvature radii of the surfaces of the optical members, D (unit: mm) indicates the optical member thicknesses or the optical member intervals on the optical axis AX, N(d) indicates the refractive indexes at the d-line (wavelength 588 nm), and vd indicates the Abbe number at the d-line.

Also, Table 1 shows the specifications (various types of data) of the endoscope magnification optical system 100 according to Working Example 1. Specifically, Table 1 shows the effective F numbers, the focal lengths (unit: mm) of the entire system, the optical magnifications, the half field angles (unit: degree), the BFs (back focuses) (unit: mm), the image heights (unit: mm), and the entire lengths of the endoscope magnification optical system 100 (unit: mm). The lower left field of Table 1 shows values (various types of data) at the wide angle end, and the lower right field of Table 1 shows values (various types of data) at the telephoto end.

TABLE 1

Working Example 1

| Surface data (wide angle end) | | | | | Surface data (telephoto end) | | | | |
|---|---|---|---|---|---|---|---|---|---|
| NO | R | D | N(d) | vd | NO | R | D | N(d) | vd |
| 1 | INFINITY | 0.357 | 1.88300 | 40.8 | 1 | INFINITY | 0.357 | 1.88300 | 40.8 |
| 2 | 1.188 | 0.509 | | | 2 | 1.188 | 0.509 | | |
| 3 | 7.048 | 0.357 | 1.72916 | 54.7 | 3 | 7.048 | 0.357 | 1.72916 | 54.7 |
| 4 | 0.785 | 0.357 | 1.84666 | 23.8 | 4 | 0.785 | 0.357 | 1.84666 | 23.8 |
| 5 | 3.039 | 0.834 | Variable | | 5 | 3.039 | 0.390 | Variable | |
| 6 Aperture | INFINITY | 0.072 | | | 6 Aperture | INFINITY | 0.072 | | |
| 7 | 1.892 | 0.447 | 1.88300 | 40.8 | 7 | 1.892 | 0.447 | 1.88300 | 40.8 |
| 8 | 28.548 | 0.271 | | | 8 | 28.548 | 0.271 | | |
| 9 | 13.741 | 0.267 | 1.92286 | 18.9 | 9 | 13.741 | 0.267 | 1.92286 | 18.9 |
| 10 | 1.075 | 0.536 | 1.81600 | 46.6 | 10 | 1.075 | 0.536 | 1.81600 | 46.6 |
| 11 | −1.424 | 0.557 | Variable | | 11 | −1.424 | 1.001 | Variable | |
| 12 | −0.866 | 0.267 | 1.81600 | 46.6 | 12 | −0.866 | 0.267 | 1.81600 | 46.6 |
| 13 | −2.251 | 0.045 | | | 13 | −2.251 | 0.045 | | |
| 14 | −17.329 | 0.442 | 1.84666 | 23.8 | 14 | −17.329 | 0.442 | 1.84666 | 23.8 |
| 15 | −1.982 | 0.558 | | | 15 | −1.982 | 0.558 | | |
| 16 | INFINITY | 0.745 | 1.51407 | 73.4 | 16 | INFINITY | 0.745 | 1.51407 | 73.4 |
| 17 | INFINITY | 0.267 | 1.51000 | 64.0 | 17 | INFINITY | 0.267 | 1.51000 | 64.0 |
| 18 | INFINITY | — | | | 18 | INFINITY | — | | |

| Various types of data (wide angle end) | | | | Various types of data (telephoto end) | | | |
|---|---|---|---|---|---|---|---|
| F number | 8.0 | Focal length | 1.00 | F number | 9.0 | Focal length | 1.24 |
| Magnification | −0.078 | | | Magnification | −0.403 | | |
| Half field angle | 67.7 | BF | 0.07 | Half field angle | 44.8 | BF | 0.07 |
| Image height | 1.00 | Entire lens length | 6.96 | Image height | 1.00 | Entire lens length | 6.96 |

Figure 3:
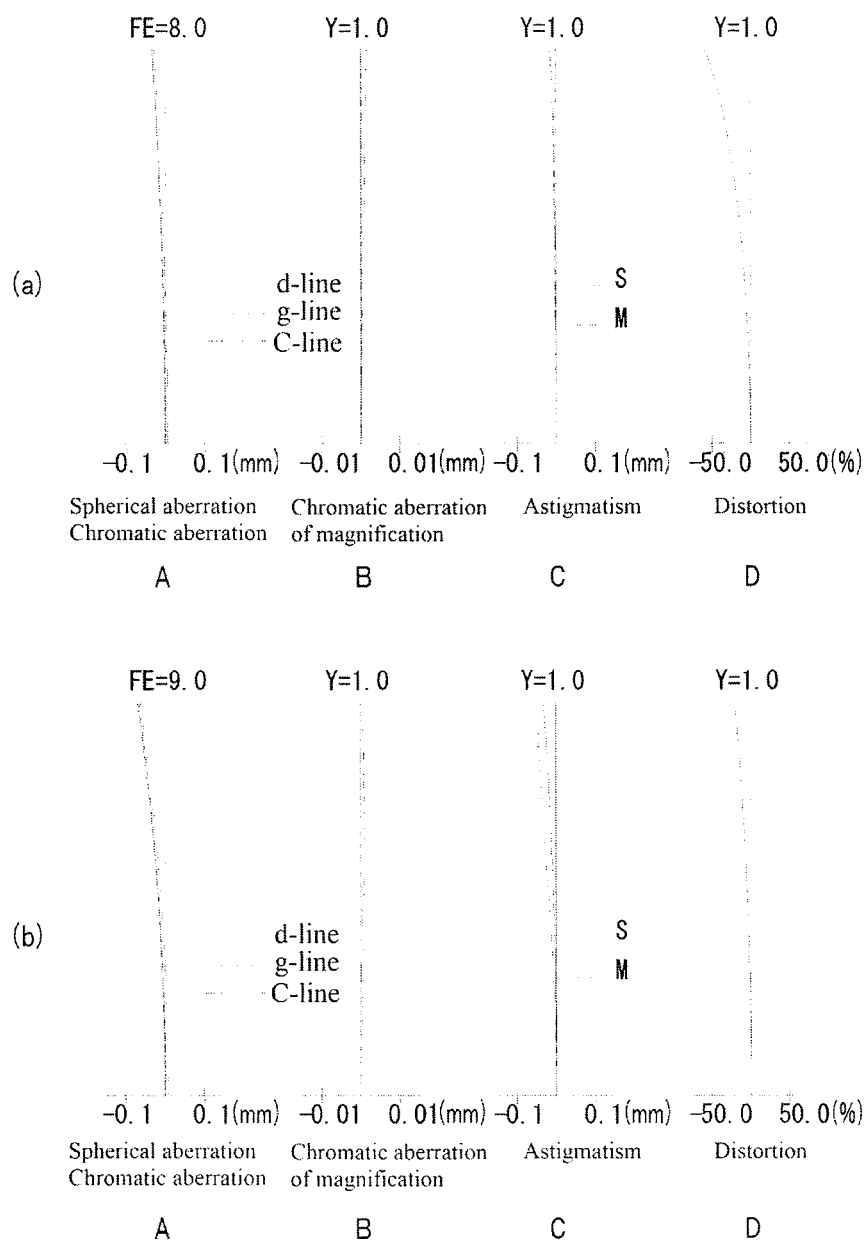
FIG. 3 is a diagram showing various aberrations in the endoscope magnification optical system according to Working Example 1 of the present invention.

Graphs A to D in FIG. 3(*a*) are diagrams of various aberrations at the time when the magnification position is at the wide angle end in the endoscope magnification optical system 100 according to Working Example 1. Graphs A to D in FIG. 3(*b*) are diagrams of various aberrations at the time when the magnification position is at the telephoto end in the endoscope magnification optical system 100 according to Working Example 1. Graphs A in FIGS. 3(*a*) and 3(*b*) show spherical aberrations and axial chromatic aberrations at the d-line, g-line (wavelength: 436 nm), and C-line (wavelength: 656 nm). Graphs B in FIGS. 3(*a*) and 3(*b*) show magnification chromatic aberrations at the d-line, g-line, and C-line. In graphs A and B, the solid lines indicate aberrations at the d-line, the dotted lines indicate aberrations at the g-line, and the one-dot chain lines indicate aberrations at the C-line. Graphs C in FIGS. 3(*a*) and 3(*b*) show astigmatisms. In graphs C, the solid lines indicate sagittal components, and the dotted lines indicate meridional components. Graphs D in FIGS. 3(*a*) and 3(*b*) show distortion. The vertical axes of graphs A to C indicate the image height, and the horizontal axes indicate the aberration amount. The vertical axes of graphs D indicate the image height, and the horizontal axes indicate the distortion rate. Note that in the central region between the wide angle end and the telephoto end, the various aberrations change within the ranges indicated by FIGS. 3(*a*) and 3(*b*). Also, the description of the tables and diagrams of Working Example 1 also apply to the tables and diagrams presented in the following numerical working examples.

As can be understood from FIGS. 2 and 3 and Table 1, although the endoscope magnification optical system 100 according to Working Example 1 is small, the optical performance (in particular, correction of astigmatism, a comatic aberration, and a chromatic aberration) is favorable at every magnification position from the wide angle end to the telephoto end.

Working Example 2

FIGS. 4(a) and 4(b) are cross-sectional views showing an arrangement of the endoscope magnification optical system 100 according to Working Example 2 of the present invention and optical components arranged downstream thereof. FIG. 4(a) is a cross-sectional view showing a lens arrangement when the magnification position is at the wide angle end. FIG. 4(b) is a cross-sectional view showing a lens arrangement for when the magnification position is at the telephoto end.

Figure 4:
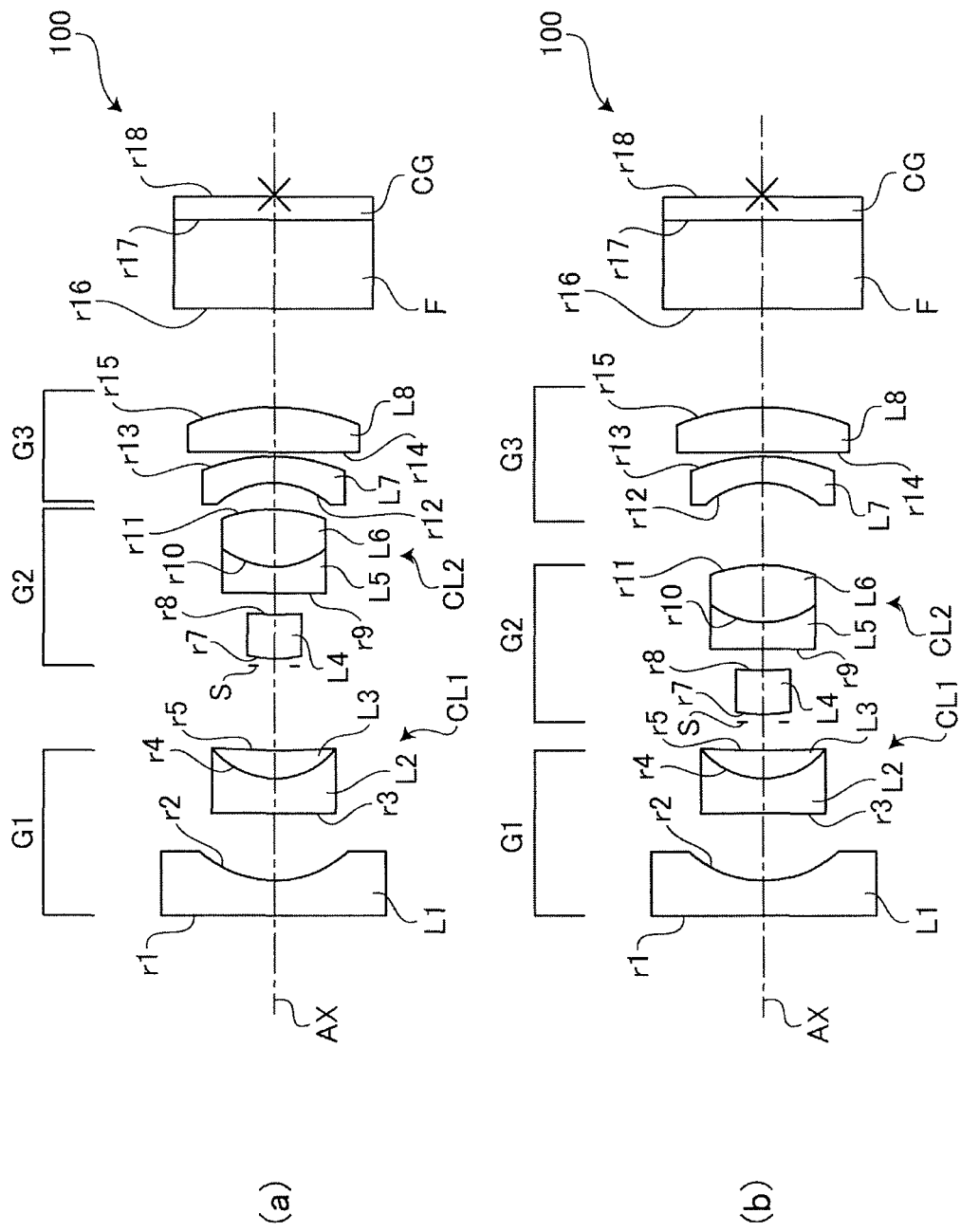
FIG. 4 is a lens arrangement diagram showing a configuration of an endoscope magnification optical system according to Working Example 2 of the present invention.

As shown in FIG. 4, the endoscope magnification optical system 100 according to Working Example 2 has the same lens configuration as the endoscope magnification optical system 100 according to Working Example 1.

Graphs A to D in FIG. 5(a) are diagrams of various aberrations at the time when the magnification position is at the wide angle end in the endoscope magnification optical system 100 according to Working Example 2. Graphs A to D in FIG. 5(b) are diagrams of various aberrations at the time when the magnification position is at the telephoto end in the endoscope magnification optical system 100 according to Working Example 2.

Table 2 shows a specific numerical value configuration and specifications of the optical components included in the endoscope magnification optical system 100 according to Working Example 2.

Figure 5:
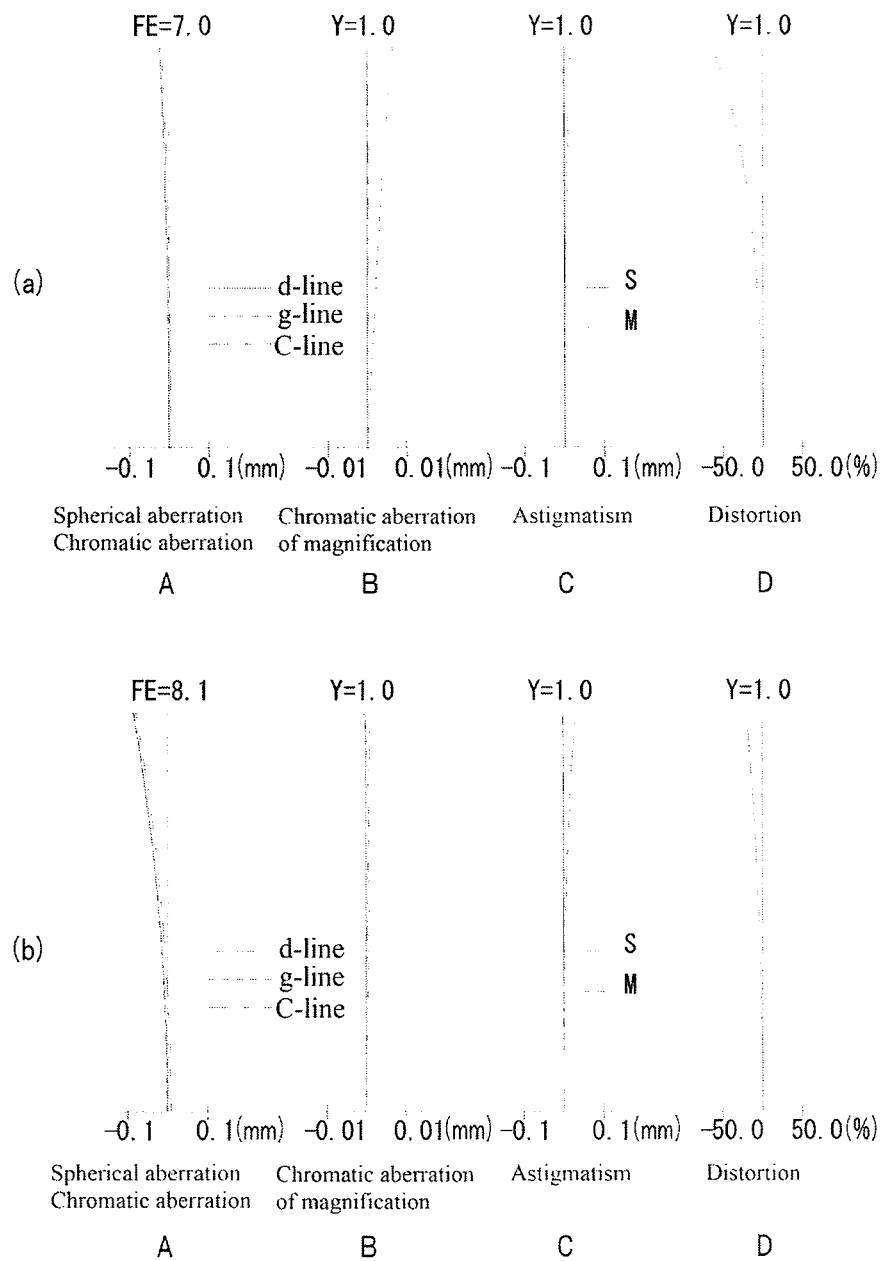
FIG. 5 is a diagram showing various aberrations in the endoscope magnification optical system according to Working Example 2 of the present invention.

As can be understood from FIGS. 4 and 5 and Table 2, although the endoscope magnification optical system 100 according to Working Example 2 is small, the optical performance (in particular, correction of astigmatism, a comatic aberration, and a chromatic aberration) is favorable at every magnification position from the wide angle end to the telephoto end.

Working Example 3

FIGS. 6(a) and 6(b) are cross-sectional views showing an arrangement of the endoscope magnification optical system 100 according to Working Example 3 of the present invention and optical components arranged downstream thereof. FIG. 6(a) is a cross-sectional view showing a lens arrangement when the magnification position is at the wide angle end. FIG. 6(b) is a cross-sectional view showing a lens arrangement for when the magnification position is at the telephoto end.

Figure 6:
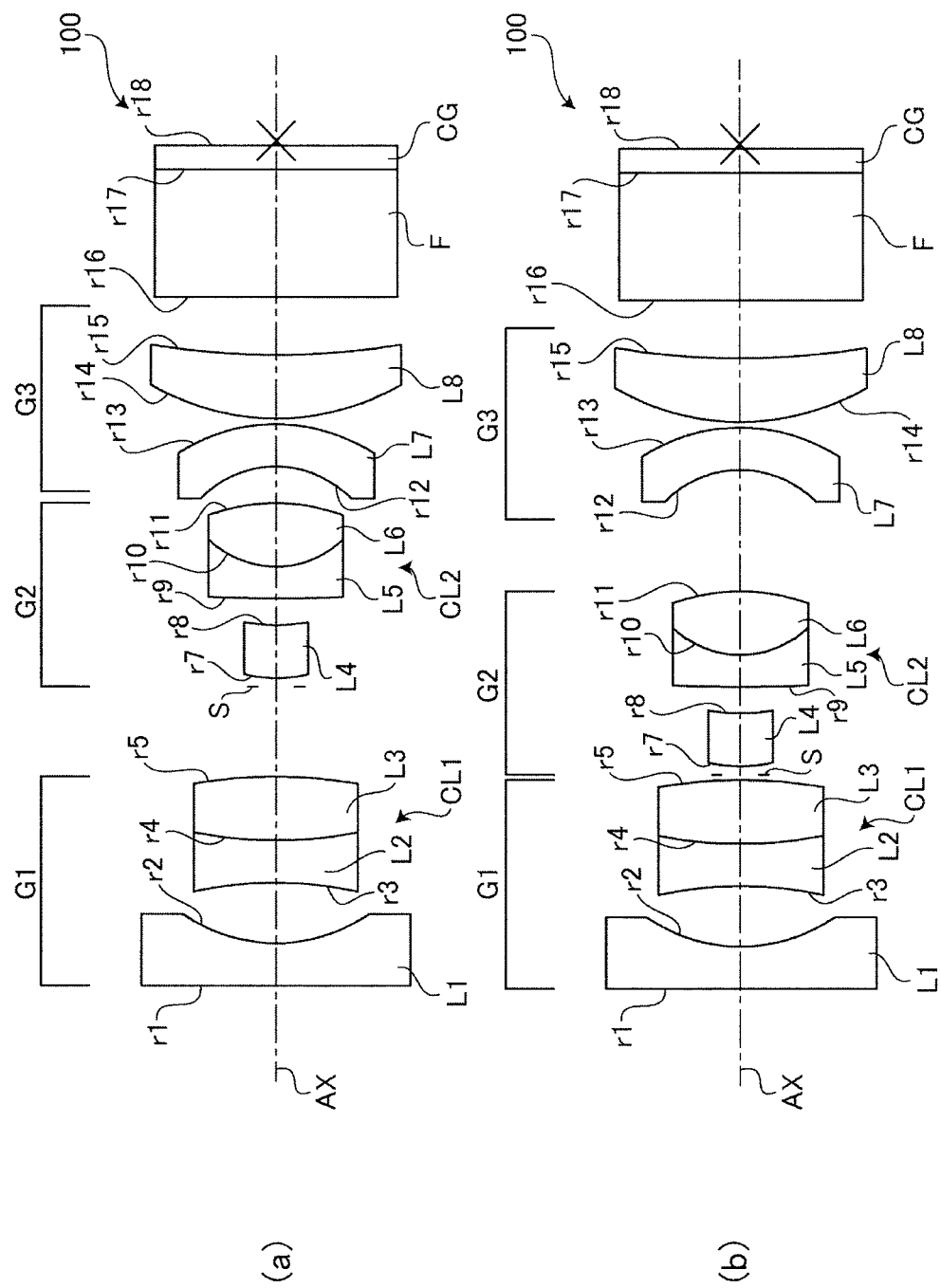
FIG. 6 is a lens arrangement diagram showing a configuration of an endoscope magnification optical system according to Working Example 3 of the present invention.

As shown in FIG. 6, the endoscope magnification optical system 100 according to Working Example 3 has the same lens configuration as the endoscope magnification optical system 100 according to Working Example 1. Graphs A to D in FIG. 7(a) are diagrams of various aberrations at the time when the magnification position is at the wide angle end in the endoscope magnification optical system 100 according to Working Example 3. Graphs A to D in FIG. 7(b) are diagrams of various aberrations at the time when the magnification position is at the telephoto end in the endoscope magnification optical system 100 according to Working Example 3.

Table 3 shows a specific numerical value configuration and specifications of the optical components included in the endoscope magnification optical system 100 according to Working Example 3.

TABLE 2

Working Example 2

| | Surface data (wide angle end) | | | | | Surface data (telephoto end) | | | |
|---|---|---|---|---|---|---|---|---|---|
| NO | R | D | N(d) | vd | NO | R | D | N(d) | vd |
| 1 | INFINITY | 0.348 | 1.88300 | 40.8 | 1 | INFINITY | 0.348 | 1.88300 | 40.8 |
| 2 | 1.119 | 0.657 | | | 2 | 1.119 | 0.657 | | |
| 3 | INFINITY | 0.348 | 1.72916 | 54.7 | 3 | INFINITY | 0.348 | 1.72916 | 54.7 |
| 4 | 0.804 | 0.278 | 1.84666 | 23.8 | 4 | 0.804 | 0.278 | 1.84666 | 23.8 |
| 5 | 9.450 | 0.830 | Variable | | 5 | 9.450 | 0.280 | Variable | |
| 6 Aperture | INFINITY | 0.075 | | | 6 Aperture | INFINITY | 0.075 | | |
| 7 | 1.433 | 0.435 | 1.88300 | 40.8 | 7 | 1.433 | 0.435 | 1.88300 | 40.8 |
| 8 | 4.916 | 0.212 | | | 8 | 4.916 | 0.212 | | |
| 9 | INFINITY | 0.261 | 1.92286 | 18.9 | 9 | INFINITY | 0.261 | 1.92286 | 18.9 |
| 10 | 0.854 | 0.565 | 1.81600 | 46.6 | 10 | 0.854 | 0.565 | 1.81600 | 46.6 |
| 11 | −1.519 | 0.261 | Variable | | 11 | −1.519 | 0.811 | Variable | |
| 12 | −0.871 | 0.261 | 1.81600 | 46.6 | 12 | −0.871 | 0.261 | 1.81600 | 46.6 |
| 13 | −1.875 | 0.044 | | | 13 | −1.875 | 0.044 | | |
| 14 | INFINITY | 0.443 | 1.84666 | 23.8 | 14 | INFINITY | 0.443 | 1.84666 | 23.8 |
| 15 | −2.220 | 0.970 | | | 15 | −2.220 | 0.970 | | |
| 16 | INFINITY | 0.870 | 1.51407 | 73.4 | 16 | INFINITY | 0.870 | 1.51407 | 73.4 |
| 17 | INFINITY | 0.227 | 1.51000 | 63.0 | 17 | INFINITY | 0.227 | 1.51000 | 63.0 |
| 18 | INFINITY | — | | | 18 | INFINITY | — | | |

| Various types of data (wide angle end) | | | | Various types of data (telephoto end) | | | |
|---|---|---|---|---|---|---|---|
| F number | 7.0 | Focal length | 0.99 | F number | 8.1 | Focal length | 1.28 |
| Magnification | −0.062 | | | Magnification | −0.408 | | |
| Half field angle | 71.4 | BF | 0.027 | Half field angle | 43.9 | BF | 0.027 |
| Image height | 1.00 | Entire lens length | 7.11 | Image height | 1.00 | Entire lens length | 7.11 |

TABLE 3

Working Example 3

| | Surface data (wide angle end) | | | | | Surface data (telephoto end) | | | |
|---|---|---|---|---|---|---|---|---|---|
| NO | R | D | N(d) | vd | NO | R | D | N(d) | vd |
| 1 | INFINITY | 0.440 | 1.88300 | 40.8 | 1 | INFINITY | 0.440 | 1.88300 | 40.8 |
| 2 | 1.766 | 0.627 | | | 2 | 1.766 | 0.627 | | |
| 3 | −4.105 | 0.440 | 1.72916 | 54.7 | 3 | −4.105 | 0.440 | 1.72916 | 54.7 |
| 4 | 4.637 | 0.660 | 1.92286 | 18.9 | 4 | 4.637 | 0.660 | 1.92286 | 18.9 |
| 5 | −5.327 | 0.935 | Variable | | 5 | −5.327 | 0.055 | Variable | |
| 6 Aperture | INFINITY | 0.088 | | | 6 Aperture | INFINITY | 0.088 | | |
| 7 | 1.481 | 0.550 | 1.88300 | 40.8 | 7 | 1.481 | 0.550 | 1.88300 | 40.8 |
| 8 | 1.956 | 0.275 | | | 8 | 1.956 | 0.275 | | |
| 9 | 14.462 | 0.330 | 1.92286 | 18.9 | 9 | 14.462 | 0.330 | 1.92286 | 18.9 |
| 10 | 1.040 | 0.660 | 1.88300 | 40.8 | 10 | 1.040 | 0.660 | 1.88300 | 40.8 |
| 11 | −2.112 | 0.381 | Variable | | 11 | −2.112 | 1.261 | Variable | |
| 12 | −1.130 | 0.440 | 1.88300 | 40.8 | 12 | −1.130 | 0.440 | 1.88300 | 40.8 |
| 13 | −1.923 | 0.057 | | | 13 | −1.923 | 0.057 | | |
| 14 | 2.667 | 0.660 | 1.84666 | 23.8 | 11 | 2.667 | 0.660 | 1.84666 | 23.8 |
| 15 | 8.298 | 0.600 | | | 15 | 8.298 | 0.600 | | |
| 16 | INFINITY | 1.320 | 1.51407 | 73.4 | 16 | INFINITY | 1.320 | 1.51407 | 73.4 |
| 17 | INFINITY | 0.250 | 1.51000 | 63.0 | 17 | INFINITY | 0.250 | 1.51000 | 63.0 |
| 18 | INFINITY | — | | | 18 | INFINITY | — | | |

| Various types of data (wide angle end) | | | | Various types of data (telephoto end) | | | |
|---|---|---|---|---|---|---|---|
| F number | 7.0 | Focal length | 1.32 | F number | 8.5 | Focal length | 1.67 |
| Magnification | −0.095 | | | Magnification | −0.572 | | |
| Half field angle | 72.3 | BF | 0.047 | Half field angle | 43.0 | BF | 0.047 |
| Image height | 1.27 | Entire lens length | 8.76 | Image height | 1.27 | Entire lens length | 8.76 |

Figure 7:
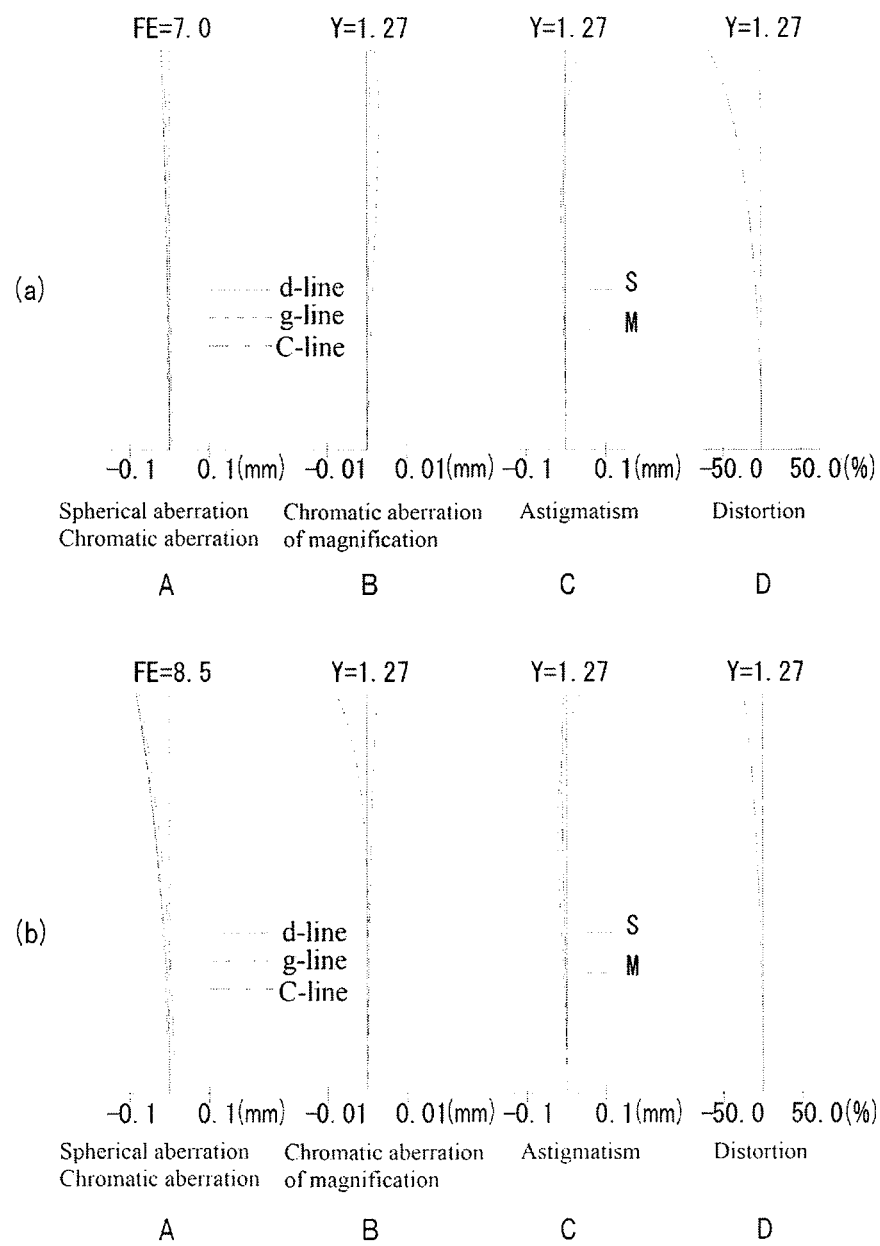
FIG. 7 is a diagram showing various aberrations in the endoscope magnification optical system according to Working Example 3 of the present invention.

As can be understood from FIGS. 6 and 7 and Table 3, although the endoscope magnification optical system 100 according to Working Example 3 is small, the optical performance (in particular, correction of astigmatism, comatic aberration, and chromatic aberration) is favorable at every magnification position from the wide angle end to the telephoto end.

Working Example 4

FIGS. 8(a) and 8(b) are cross-sectional views showing an arrangement of the endoscope magnification optical system 100 according to Working Example 4 of the present invention and optical components arranged downstream thereof. FIG. 8(a) is a cross-sectional view showing a lens arrangement when the magnification position is at the wide angle end. FIG. 8(b) is a cross-sectional view showing a lens arrangement for when the magnification position is at the telephoto end.

Figure 8:
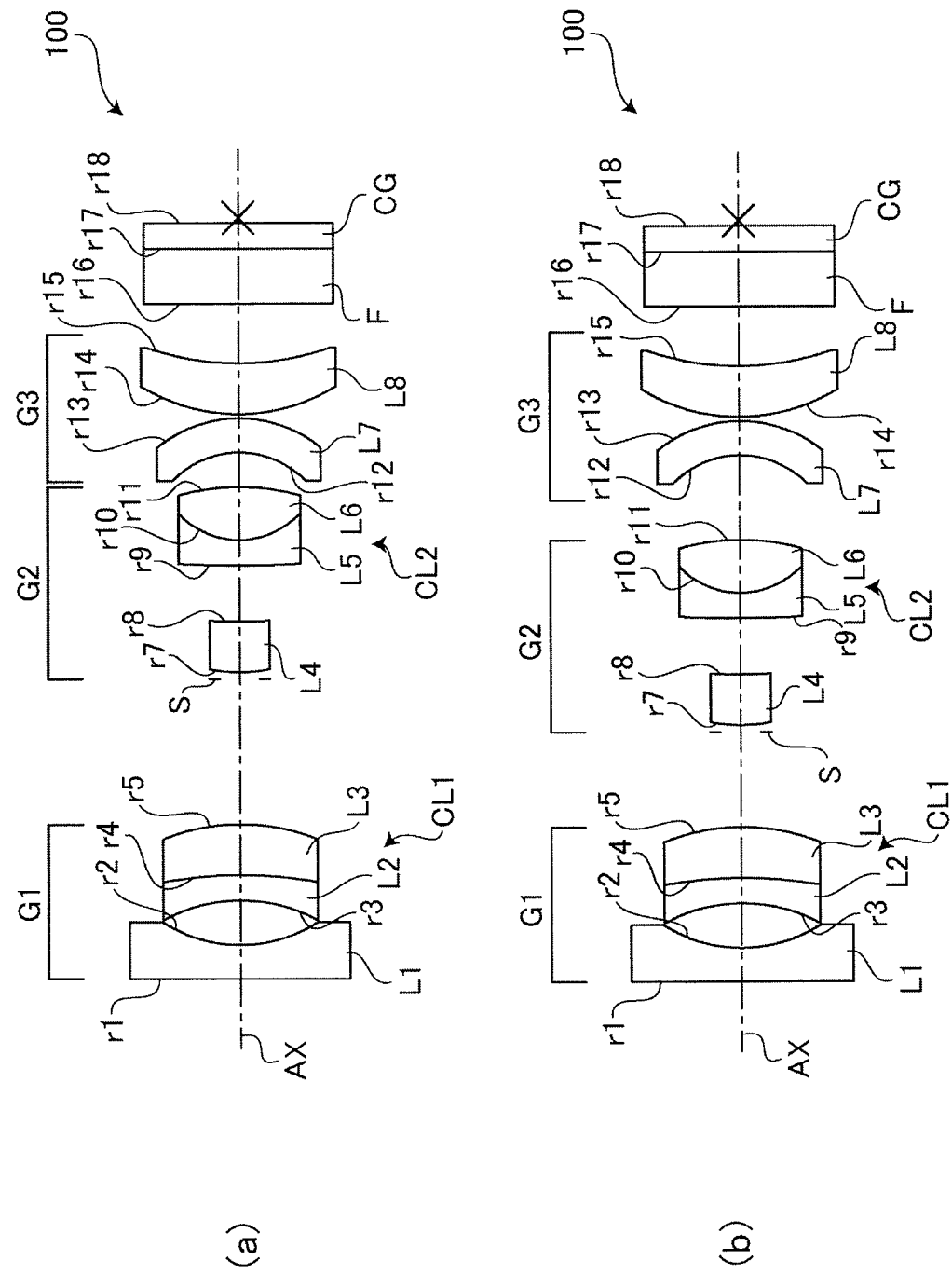
FIG. 8 is a lens arrangement diagram showing a configuration of an endoscope magnification optical system according to Working Example 4 of the present invention.

As shown in FIG. 8, the endoscope magnification optical system 100 according to Working Example 4 has the same lens configuration as the endoscope magnification optical system 100 according to Working Example 1. Graphs A to D in FIG. 9(a) are diagrams of various aberrations at the time when the magnification position is at the wide angle end in the endoscope magnification optical system 100 according to Working Example 4. Graphs A to D in FIG. 9(b) are diagrams of various aberrations at the time when the magnification position is at the telephoto end in the endoscope magnification optical system 100 according to Working Example 4.

Table 4 shows a specific numerical value configuration and specifications of the optical components included in the endoscope magnification optical system 100 according to Working Example 4.

TABLE 4

Working Example 4

| | Surface data (wide angle end) | | | | | Surface data (telephoto end) | | | |
|---|---|---|---|---|---|---|---|---|---|
| NO | R | D | N(d) | vd | NO | R | D | N(d) | vd |
| 1 | INFINITY | 0.484 | 1.88300 | 40.8 | 1 | INFINITY | 0.484 | 1.88300 | 40.8 |
| 2 | 2.180 | 0.634 | | | 2 | 2.180 | 0.634 | | |
| 3 | −2.420 | 0.363 | 1.77250 | 49.6 | 3 | −2.420 | 0.363 | 1.77250 | 49.6 |
| 4 | −6.561 | 0.726 | 1.84666 | 23.8 | 4 | −6.561 | 0.726 | 1.84666 | 23.8 |
| 5 | −3.132 | 2.079 | Variable | | 5 | −3.132 | 1.362 | Variable | |
| 6 Aperture | INFINITY | 0.097 | | | 6 Aperture | INFINITY | 0.097 | | |
| 7 | 2.319 | 0.726 | 1.88300 | 40.8 | 7 | 2.319 | 0.726 | 1.88300 | 40.8 |
| 8 | 7.116 | 0.804 | | | 8 | 7.116 | 0.804 | | |
| 9 | 16.804 | 0.363 | 1.84666 | 23.8 | 9 | 16.804 | 0.363 | 1.84666 | 23.8 |
| 10 | 1.246 | 0.757 | 1.77250 | 49.6 | 10 | 1.246 | 0.757 | 1.77250 | 49.6 |
| 11 | −3.387 | 0.496 | Variable | | 11 | −3.387 | 1.213 | Variable | |
| 12 | −1.384 | 0.484 | 1.81600 | 46.6 | 12 | −1.384 | 0.484 | 1.81600 | 46.6 |
| 13 | −1.964 | 0.061 | | | 13 | −1.964 | 0.061 | | |
| 14 | 2.802 | 0.726 | 1.84666 | 23.8 | 14 | 2.802 | 0.726 | 1.84666 | 23.8 |

TABLE 4-continued

| | | Working Example 4 | | | | | | | |
|---|---|---|---|---|---|---|---|---|---|
| 15 | 4.195 | 0.852 | | | 15 | 4.195 | 0.852 | | |
| 16 | INFINITY | 0.786 | 1.51407 | 73.4 | 16 | INFINITY | 0.786 | 1.51407 | 73.4 |
| 17 | INFINITY | 0.363 | 1.51000 | 63.0 | 17 | INFINITY | 0.363 | 1.51000 | 63.0 |
| 18 | INFINITY | — | | | 18 | INFINITY | — | | |

| Various types of data (wide angle end) | | | | Various types of data (telephoto end) | | | |
|---|---|---|---|---|---|---|---|
| F number | 6.1 | Focal length | 1.43 | F number | 6.9 | Focal length | 1.67 |
| Magnification | −0.094 | | | Magnification | −0.414 | | |
| Half field angle | 71.3 | BF | 0.074 | Half field angle | 49.2 | BF | 0.074 |
| Image height | 42.83 | Entire lens length | 10.87 | Image height | 1.39 | Entire lens length | 10.88 |

Figure 9:
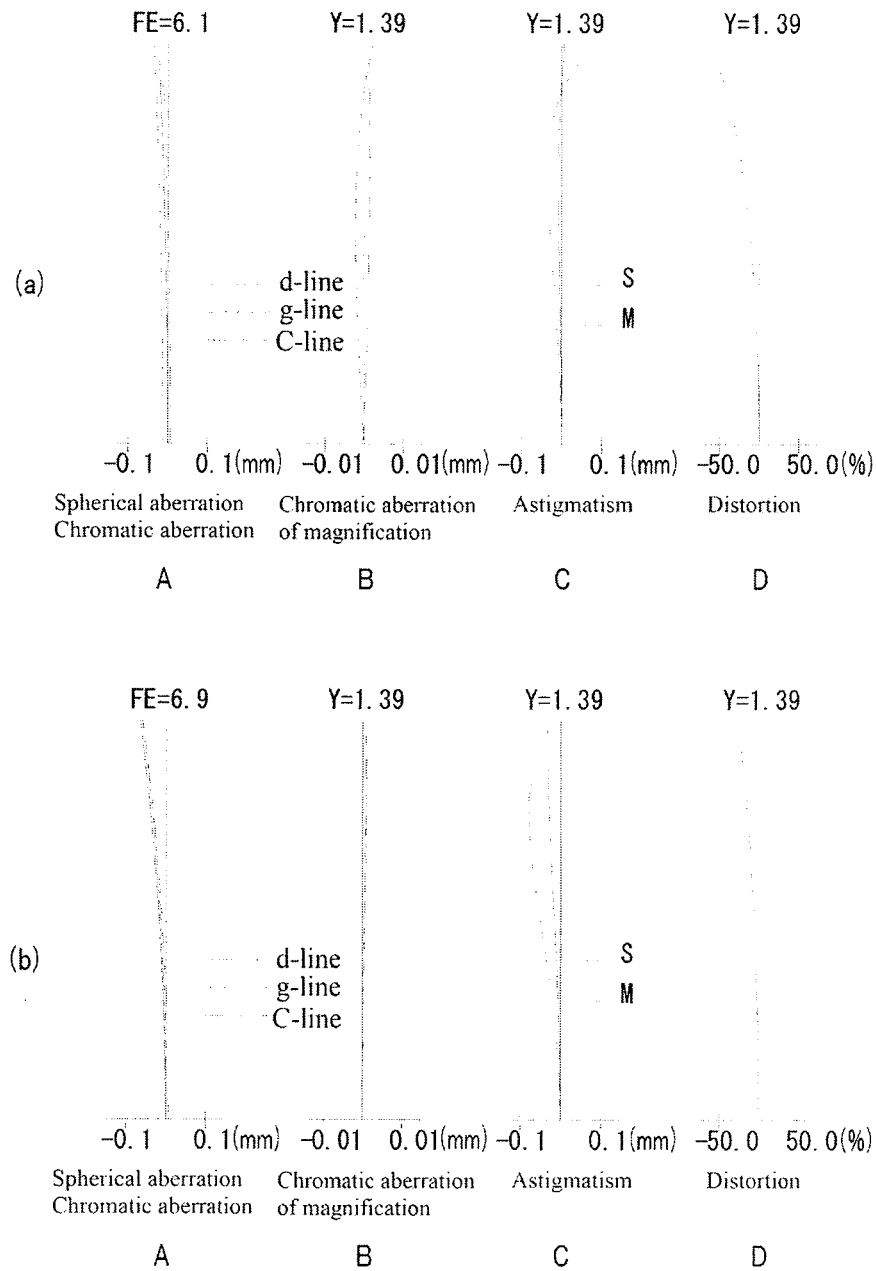
FIG. 9 is a diagram showing various aberrations in the endoscope magnification optical system according to Working Example 4 of the present invention.

As can be understood from FIGS. 8 and 9 and Table 4, although the endoscope magnification optical system 100 according to Working Example 4 is small, the optical performance (in particular, correction of astigmatism, comatic aberration, and chromatic aberration) is favorable at every magnification position from the wide angle end to the telephoto end.

Working Example 5

FIGS. 10(a) and 10(b) are cross-sectional views showing an arrangement of the endoscope magnification optical system 100 according to Working Example 5 of the present invention and optical components arranged downstream thereof. FIG. 10(a) is a cross-sectional view showing a lens arrangement for when the magnification position is at the wide angle end. FIG. 10(b) is a cross-sectional view showing a lens arrangement for when the magnification position is at the telephoto end.

Figure 10:
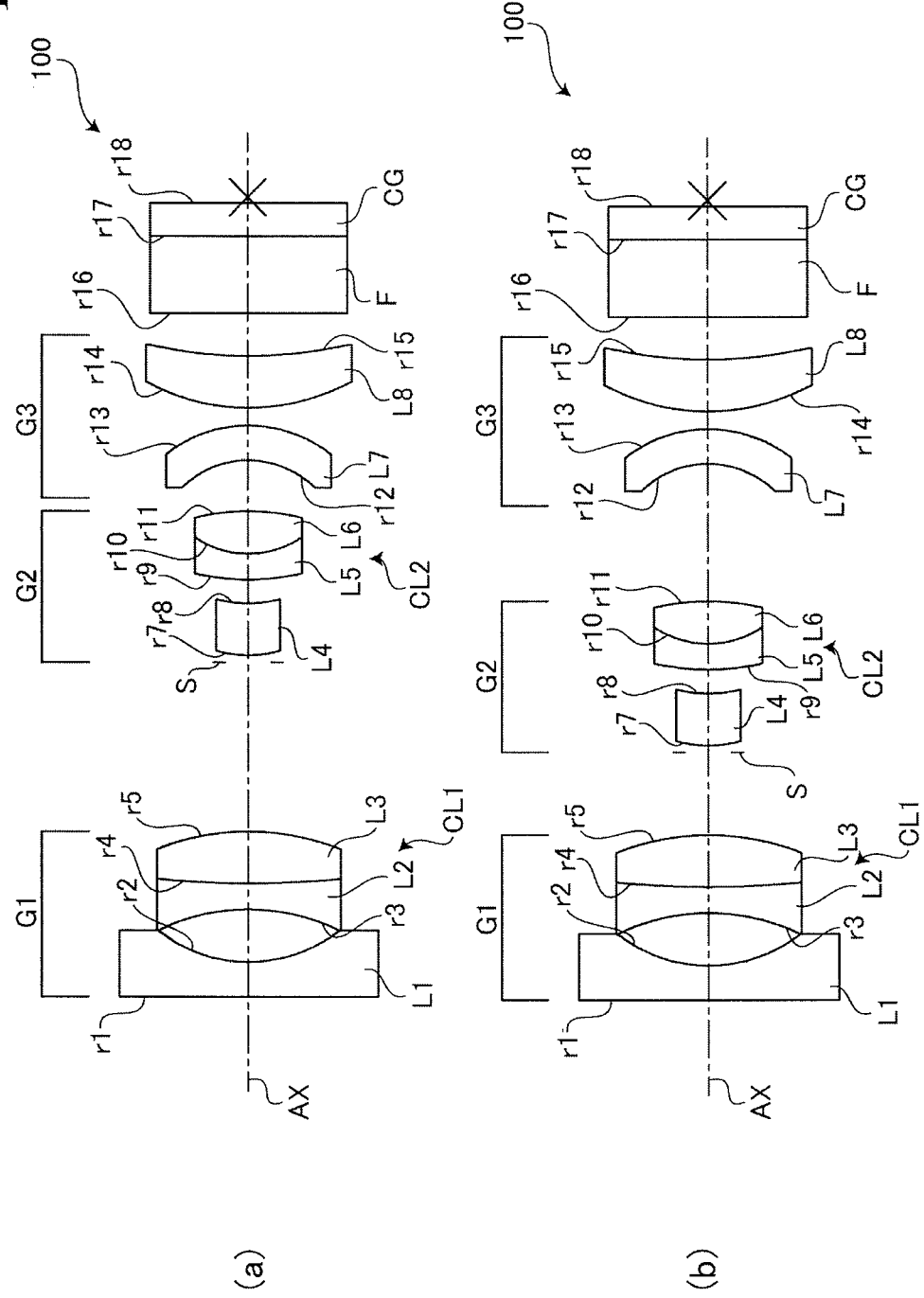
FIG. 10 is a lens arrangement diagram showing a configuration of an endoscope magnification optical system according to Working Example 5 of the present invention.

As shown in FIG. 10, the endoscope magnification optical system 100 according to Working Example 5 has the same lens configuration as the endoscope magnification optical system 100 according to Working Example 1.

Graphs A to D in FIG. 11(a) are diagrams of various aberrations at the time when the magnification position is at the wide angle end in the endoscope magnification optical system 100 according to Working Example 5. Graphs A to D in FIG. 11(b) are diagrams of various aberrations at the time when the magnification position is at the telephoto end in the endoscope magnification optical system 100 according to Working Example 5.

Table 5 shows a specific numerical value configuration and specifications of the optical components included in the endoscope magnification optical system 100 according to Working Example 5.

TABLE 5

| | | Working Example 5 | | | | | | | |
|---|---|---|---|---|---|---|---|---|---|
| | Surface data (wide angle end) | | | | | Surface data (telephoto end) | | | |
| NO | R | D | N(d) | vd | NO | R | D | N(d) | vd |
| 1 | INFINITY | 0.364 | 1.88300 | 40.8 | 1 | INFINITY | 0.364 | 1.88300 | 40.8 |
| 2 | 1.584 | 0.552 | | | 2 | 1.584 | 0.552 | | |
| 3 | −2.222 | 0.273 | 1.77250 | 49.6 | 3 | −2.222 | 0.273 | 1.77250 | 49.6 |
| 4 | 10.497 | 0.546 | 1.84666 | 23.8 | 4 | 10.497 | 0.546 | 1.84666 | 23.8 |
| 5 | −2.655 | 1.778 | Variable | | 5 | −2.655 | 0.868 | Variable | |
| 6 Aperture | INFINITY | 0.073 | | | 6 Aperture | INFINITY | 0.073 | | |
| 7 | 1.256 | 0.546 | 1.88300 | 40.8 | 7 | 1.256 | 0.546 | 1.88300 | 40.8 |
| 8 | 1.344 | 0.250 | | | 8 | 1.344 | 0.250 | | |
| 9 | 2.564 | 0.273 | 1.92286 | 18.9 | 9 | 2.564 | 0.273 | 1.92286 | 18.9 |
| 10 | 1.036 | 0.446 | 1.72916 | 54.7 | 10 | 1.036 | 0.446 | 1.72916 | 54.7 |
| 11 | −2.460 | 0.537 | Variable | | 11 | −2.460 | 1.447 | Variable | |
| 12 | −1.018 | 0.364 | 1.81600 | 46.6 | 12 | −1.018 | 0.364 | 1.81600 | 46.6 |
| 13 | −1.438 | 0.187 | | | 13 | −1.438 | 0.187 | | |
| 14 | 2.319 | 0.546 | 1.84666 | 23.8 | 14 | 2.319 | 0.546 | 1.84666 | 23.8 |
| 15 | 4.873 | 0.444 | | | 15 | 4.873 | 0.444 | | |
| 16 | INFINITY | 0.810 | 1.51407 | 73.4 | 16 | INFINITY | 0.810 | 1.51407 | 73.4 |
| 17 | INFINITY | 0.346 | 1.51000 | 63.0 | 17 | INFINITY | 0.346 | 1.51000 | 63.0 |
| 18 | INFINITY | — | | | 18 | INFINITY | — | | |

| Various types of data (wide angle end) | | | | Various types of data (telephoto end) | | | |
|---|---|---|---|---|---|---|---|
| F number | 5.6 | Focal length | 1.06 | F number | 7.0 | Focal length | 1.44 |
| Magnification | −0.096 | | | Magnification | −0.539 | | |
| Half field angle | 71.6 | BF | 0.065 | Half field angle | 40.6 | BF | 0.065 |
| Image height | 1.05 | Entire lens length | 8.40 | Image height | 1.05 | Entire lens length | 8.40 |

Figure 11:
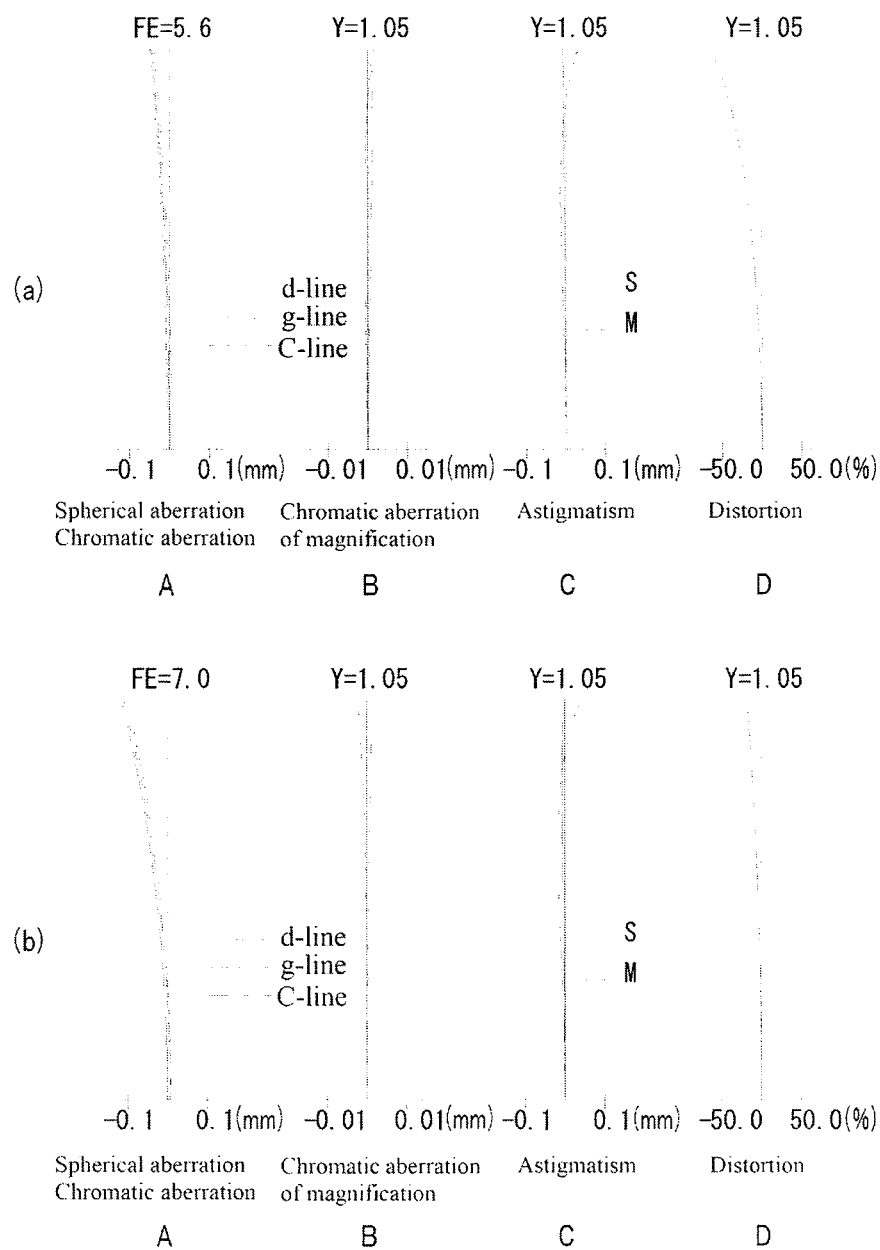
FIG. 11 is a diagram showing various aberrations in the endoscope magnification optical system according to Working Example 5 of the present invention.

As can be understood from FIGS. 10 and 11 and Table 5, although the endoscope magnification optical system 100 according to Working Example 5 is small, the optical performance (in particular, correction of astigmatism, comatic aberration, and chromatic aberration) is favorable at every magnification position from the wide angle end to the telephoto end.

Working Example 6

FIGS. 12(a) and 12(b) are cross-sectional views showing an arrangement of the endoscope magnification optical system 100 according to Working Example 6 of the present invention and optical components arranged downstream thereof. FIG. 12(a) is a cross-sectional view showing a lens arrangement for when the magnification position is at the wide angle end. FIG. 12(b) is a cross-sectional view showing a lens arrangement for when the magnification position is at the telephoto end.

Figure 12:
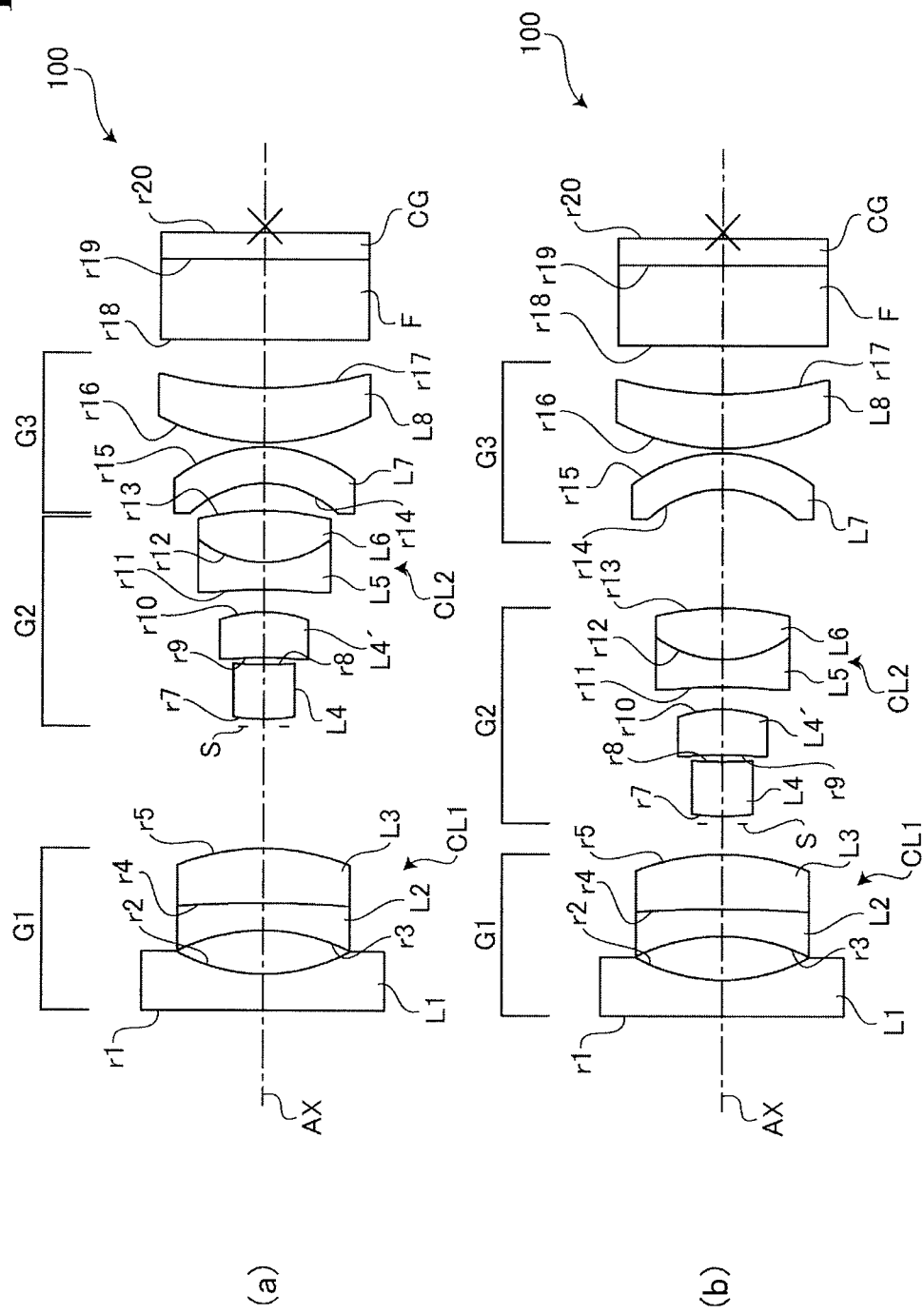
FIG. 12 is a lens arrangement diagram showing a configuration of an endoscope magnification optical system according to Working Example 6 of the present invention.

As shown in FIG. 12, the endoscope magnification optical system 100 according to Working Example 6 has the same lens configuration as the endoscope magnification optical system 100 according to Working Example 1, except for the second lens group G2.

The second lens group G2 according to Working Example 6 is a lens group that has positive power. The second lens group G2 includes at least, in order starting from the object side, a positive lens L4, a positive lens L4', and a doublet CL2 that has positive power and is obtained by bonding a negative lens L5 and a positive lens L6. In the doublet CL2, a negative lens and a positive lens may be aligned in the stated order starting from the object side, or a positive lens and a negative lens may be aligned in the stated order starting from the object side.

In order to reduce the size of the endoscope magnification optical system 100, it is necessary to give a strong power to the second lens group G2, which is a moving lens group. However, by merely strengthening the power of the second lens group G2, there is a risk that the optical performance will deteriorate (here, in particular, the eccentric sensitivity increases regarding astigmatism). In view of this, by using a configuration in which the second lens group G2 includes two positive lenses and a doublet and dividing the burden of the power between the two positive lenses, it is possible to give a strong positive power to the second lens group G2 and reduce the eccentric sensitivity in the second lens group G2.

Also, by arranging the doublet in the second lens group G2 at a location closest to the image, off-axis light beams pass through positions located away from the optical axis AX, which is advantageous for reducing chromatic aberrations of magnification.

Note that it is not necessarily better to simply include a greater number of positive lenses in the second lens group G2. For example, if the number of positive lenses in the second lens group G2 is increased to three or more, a significant effect of reducing the eccentric sensitivity is not necessarily obtained in comparison to a configuration including two positive lenses. On the contrary, increasing the number of positive lenses to three or more has significant disadvantages, such as the cost increasing due to an increase in the number of components and the overall length of the endoscope magnification optical system 100 increasing.

Also, the endoscope magnification optical system 100 according to Working Example 6 has a configuration in which the focal lengths of the two positive lenses included in the second lens group G2 are mutually different, and in the case where the composite focal length of the two positive lenses is defined as $f_c$ (unit: mm) and the longer focal length of the focal lengths of the two positive lenses is defined as $f_p$ (unit: mm), the following conditional expression (4)

$$0.3 f_c / f_p \quad (4)$$

is satisfied.

If the value on the right side of conditional expression (4) is less than or equal to the value on the left side, the burden of power will not be suitably divided between the two positive lenses (the power of one of the two positive lenses will be excessively strong), and therefore the effect of reducing the eccentric sensitivity in the second lens group G2 will be low.

Graphs A to D in FIG. 13(a) are diagrams of various aberrations at the time when the magnification position is at the wide angle end in the endoscope magnification optical system 100 according to Working Example 6. Graphs A to D in FIG. 13(b) are diagrams of various aberrations at the time when the magnification position is at the telephoto end in the endoscope magnification optical system 100 according to Working Example 6.

Table 6 shows a specific numerical value configuration and specifications of the optical components included in the endoscope magnification optical system 100 according to Working Example 6.

TABLE 6

| Working Example 6 | | | | | | | | | |
|---|---|---|---|---|---|---|---|---|---|
| Surface data (wide angle end) | | | | | Surface data (telephoto end) | | | | |
| NO | R | D | N(d) | vd | NO | R | D | N(d) | vd |
| 1 | INFINITY | 0.380 | 1.88300 | 40.8 | 1 | INFINITY | 0.380 | 1.88300 | 40.8 |
| 2 | 1.954 | 0.456 | | | 2 | 1.954 | 0.456 | | |
| 3 | −2.088 | 0.285 | 1.77250 | 49.6 | 3 | −2.088 | 0.285 | 1.77250 | 49.6 |
| 4 | −13.434 | 0.570 | 1.84666 | 23.8 | 4 | −13.434 | 0.570 | 1.84666 | 23.8 |
| 5 | −2.523 | 1.278 | Variable | | 5 | −2.523 | 0.323 | Variable | |
| 6 Aperture | INFINITY | 0.076 | | | 6 Aperture | INFINITY | 0.076 | | |
| 7 | 2.348 | 0.570 | 1.88300 | 40.8 | 7 | 2.348 | 0.570 | 1.88300 | 40.8 |
| 8 | 4.849 | 0.076 | | | 8 | 4.849 | 0.076 | | |
| 9 | −3.303 | 0.475 | 1.88300 | 40.8 | 9 | −3.303 | 0.475 | 1.88300 | 40.8 |
| 10 | −1.415 | 0.235 | | | 10 | −1.415 | 0.235 | | |
| 11 | −5.113 | 0.285 | 1.84666 | 23.8 | 11 | −5.113 | 0.285 | 1.84666 | 23.8 |
| 12 | 1.197 | 0.539 | 1.77250 | 49.6 | 12 | 1.197 | 0.539 | 1.77250 | 49.6 |
| 13 | −3.003 | 0.285 | Variable | | 13 | −3.003 | 1.240 | Variable | |
| 14 | −1.173 | 0.380 | 1.81600 | 46.6 | 14 | −1.173 | 0.380 | 1.81600 | 46.6 |
| 15 | −1.566 | 0.048 | | | 15 | −1.566 | 0.048 | | |
| 16 | 2.477 | 0.570 | 1.84666 | 23.8 | 16 | 2.477 | 0.570 | 1.84666 | 23.8 |

TABLE 6-continued

| | | Working Example 6 | | | | | | | |
|---|---|---|---|---|---|---|---|---|---|
| 17 | 4.201 | 0.500 | | | 17 | 4.201 | 0.500 | | |
| 18 | INFINITY | 0.840 | 1.51407 | 73.4 | 18 | INFINITY | 0.840 | 1.51407 | 73.4 |
| 19 | INFINITY | 0.283 | 1.51000 | 63.0 | 19 | INFINITY | 0.283 | 1.51000 | 63.0 |
| 20 | INFINITY | — | | | 20 | INFINITY | — | | |

| Various types of data (wide angle end) | | | | Various types of data (telephoto end) | | | |
|---|---|---|---|---|---|---|---|
| F number | 6.8 | Focal length | 1.12 | F number | 8.3 | Focal length | 1.49 |
| Magnification | −0.080 | | | Magnification | −0.550 | | |
| Half field angle | 77.1 | BF | 0.065 | Half field angle | 42.1 | BF | 0.065 |
| Image height | 1.12 | Entire lens length | 8.20 | Image height | 1.12 | Entire lens length | 8.20 |

Figure 13:
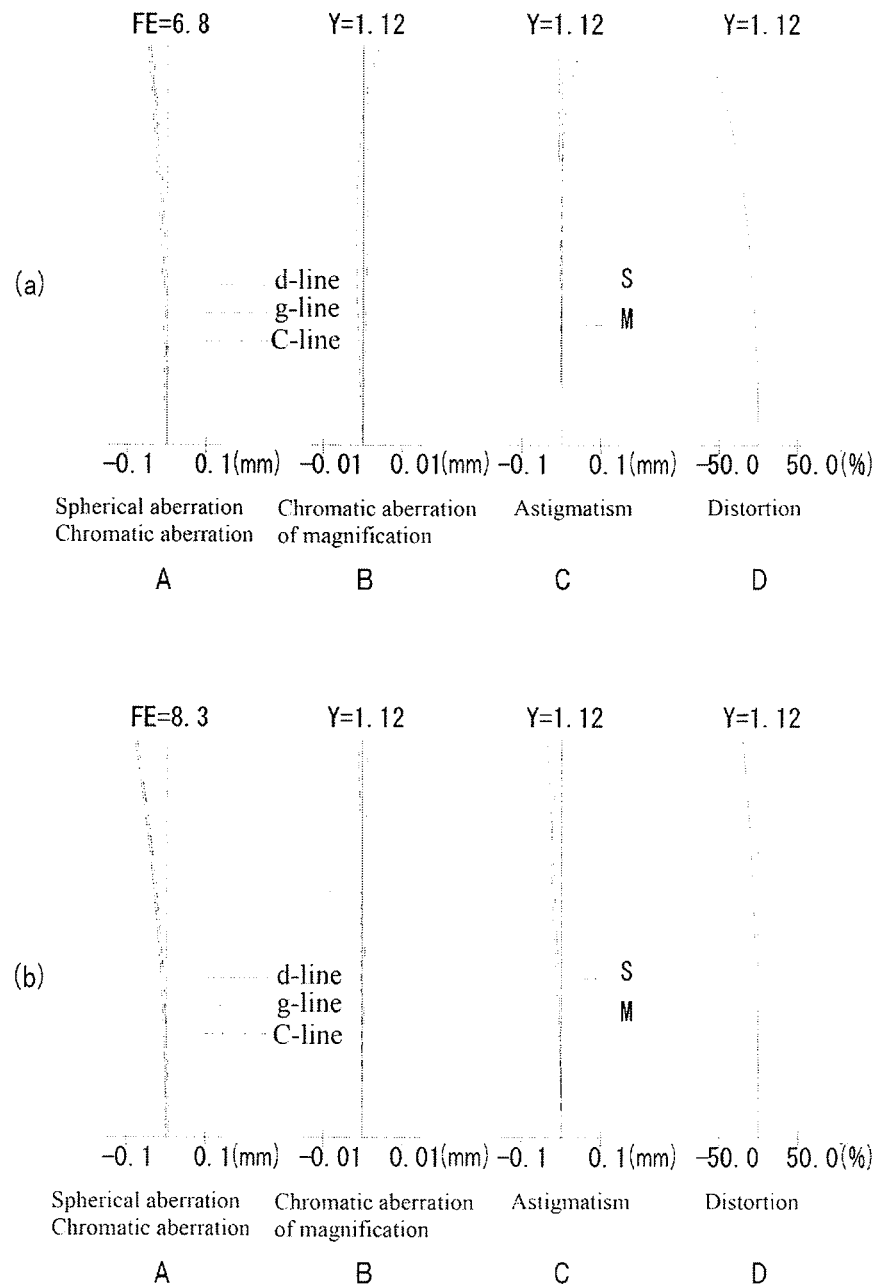
FIG. 13 is a diagram showing various aberrations in the endoscope magnification optical system according to Working Example 6 of the present invention.

As can be understood from FIGS. 12 and 13 and Table 6, although the endoscope magnification optical system 100 according to Working Example 6 is small, the optical performance (in particular, correction of astigmatism, comatic aberration, and chromatic aberration) is favorable at every magnification position from the wide angle end to the telephoto end.

Working Example 7

FIGS. 14(a) and 14(b) are cross-sectional views showing an arrangement of the endoscope magnification optical system 100 according to Working Example 7 of the present invention and optical components arranged downstream thereof. FIG. 14(a) is a cross-sectional view showing a lens arrangement for when the magnification position is at the wide angle end. FIG. 14(b) is a cross-sectional view showing a lens arrangement for when the magnification position is at the telephoto end.

Figure 14:
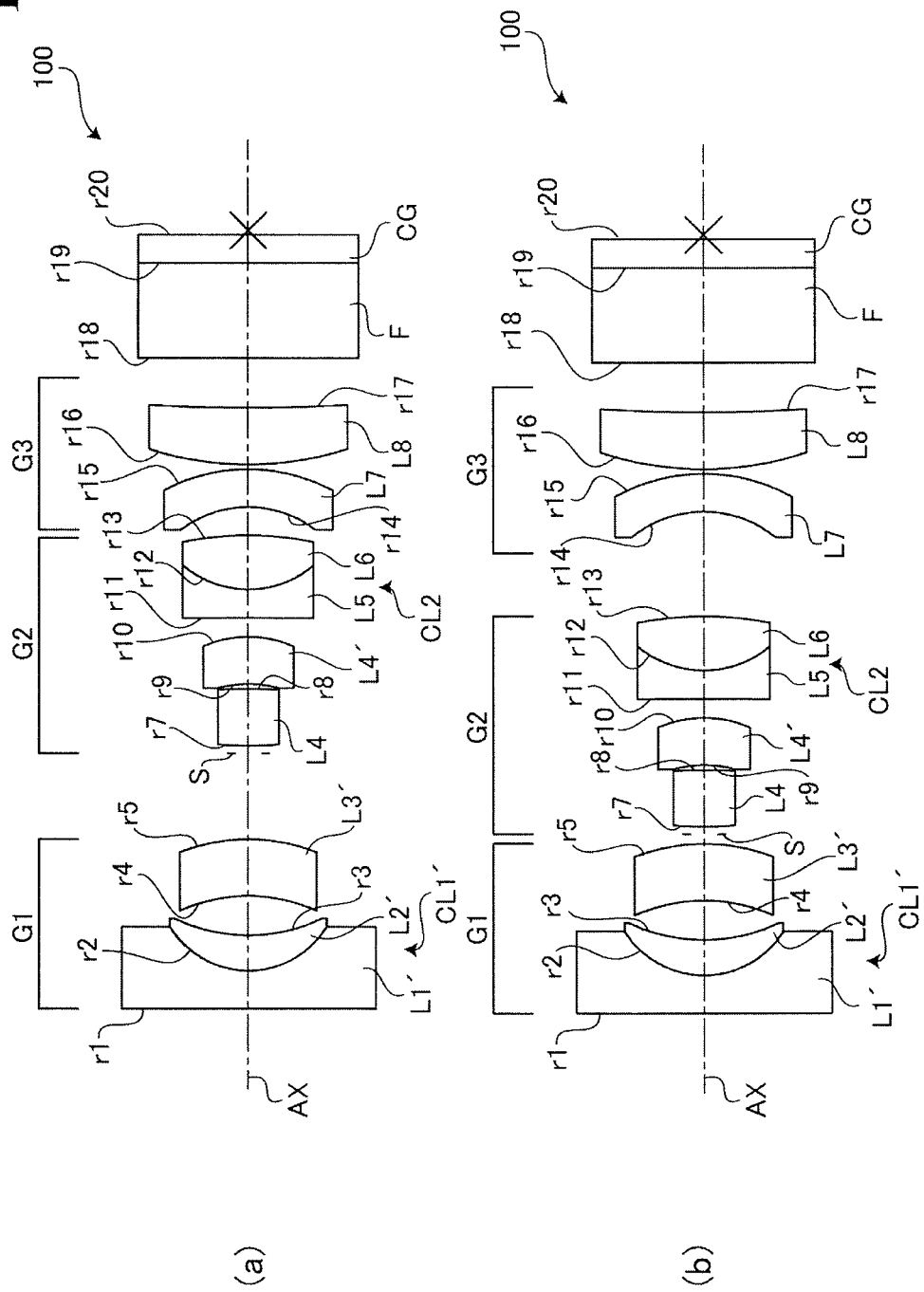
FIG. 14 is a lens arrangement diagram showing a configuration of an endoscope magnification optical system according to Working Example 7 of the present invention.

As shown in FIG. 14, the endoscope magnification optical system 100 according to Working Example 7 has the same lens configuration as the endoscope magnification optical system 100 according to Working Example 6, except for the first lens group G1.

The first lens group G1 according to Working Example 7 is a lens group that has negative power and is arranged on the object side relative to the aperture S. The first lens group G1 according to Working Example 7 includes at least, in order starting from the object side, a doublet CL1' that has negative power and is obtained by bonding a negative lens L1' and a positive lens L2', and a meniscus lens L3' with a concave surface facing the object side.

Due to the first lens group G1 having a configuration in which one single lens and one doublet (in Working Example 7, one doublet having negative power and one meniscus lens) are included, a comatic aberration and a chromatic aberration are favorably corrected in the group by dispersing the negative power in the first lens group G1 and having positive power. Accordingly, variations in aberrations in the entire system are suppressed, and aberrations are favorably suppressed at every magnification from the wide angle end to the telephoto end.

Graphs A to D in FIG. 15(a) are diagrams of various aberrations at the time when the magnification position is at the wide angle end in the endoscope magnification optical system 100 according to Working Example 7. Graphs A to D in FIG. 15(b) are diagrams of various aberrations at the time when the magnification position is at the telephoto end in the endoscope magnification optical system 100 according to Working Example 7.

Table 7 shows a specific numerical value configuration and specifications of the optical components included in the endoscope magnification optical system 100 according to Working Example 7.

TABLE 7

| | | | Working Example 7 | | | | | | |
|---|---|---|---|---|---|---|---|---|---|
| | Surface data (wide angle end) | | | | | Surface data (telephoto end) | | | |
| NO | R | D | N(d) | vd | NO | R | D | N(d) | vd |
| 1 | INFINITY | 0.473 | 1.88300 | 40.8 | 1 | INFINITY | 0.473 | 1.88300 | 40.8 |
| 2 | 1.170 | 0.442 | 1.84666 | 23.8 | 2 | 1.170 | 0.442 | 1.84666 | 23.8 |
| 3 | 2.165 | 0.490 | | | 3 | 2.165 | 0.490 | | |
| 4 | −2.128 | 0.709 | 1.84666 | 23.8 | 4 | −2.128 | 0.709 | 1.84666 | 23.8 |
| 5 | −2.381 | 1.074 | Variable | | 5 | −2.381 | 0.120 | Variable | |
| 6 Aperture | INFINITY | 0.094 | | | 6 Aperture | INFINITY | 0.094 | | |
| 7 | 3.849 | 0.709 | 1.88300 | 40.8 | 7 | 3.849 | 0.709 | 1.88300 | 40.8 |
| 8 | −5.045 | 0.059 | | | 8 | −5.045 | 0.059 | | |
| 9 | −1.485 | 0.591 | 1.88300 | 40.8 | 9 | −1.485 | 0.591 | 1.88300 | 40.8 |
| 10 | −1.416 | 0.236 | | | 10 | −1.416 | 0.236 | | |
| 11 | −36.933 | 0.355 | 1.84666 | 23.8 | 11 | −36.933 | 0.355 | 1.84666 | 23.8 |
| 12 | 1.278 | 0.675 | 1.77250 | 49.6 | 12 | 1.278 | 0.675 | 1.77250 | 49.6 |
| 13 | −4.247 | 0.355 | Variable | | 13 | −4.247 | 1.309 | Variable | |
| 14 | −1.415 | 0.473 | 1.81600 | 46.6 | 14 | −1.415 | 0.473 | 1.81600 | 46.6 |
| 15 | −2.275 | 0.059 | | | 15 | −2.275 | 0.059 | | |
| 16 | 4.140 | 0.709 | 1.84666 | 23.8 | 16 | 4.140 | 0.709 | 1.84666 | 23.8 |
| 17 | 21.595 | 0.620 | | | 17 | 21.595 | 0.620 | | |
| 18 | INFINITY | 1.182 | 1.51407 | 73.4 | 18 | INFINITY | 1.182 | 1.51407 | 73.4 |
| 19 | INFINITY | 0.355 | 1.51000 | 63.0 | 19 | INFINITY | 0.355 | 1.51000 | 63.0 |
| 20 | INFINITY | — | | | 20 | INFINITY | — | | |

TABLE 7-continued

Working Example 7

| Various types of data (wide angle end) | | | | Various types of data (telephoto end) | | | |
|---|---|---|---|---|---|---|---|
| F number | 8.0 | Focal length | 1.39 | F number | 9.4 | Focal length | 1.79 |
| Magnification | −0.124 | | | Magnification | −0.575 | | |
| Half field angle | 76.2 | BF | 0.052 | Half field angle | 42.9 | BF | 0.052 |
| Image height | 1.40 | Entire lens length | 9.71 | Image height | 1.40 | Entire lens length | 9.71 |

Figure 15:
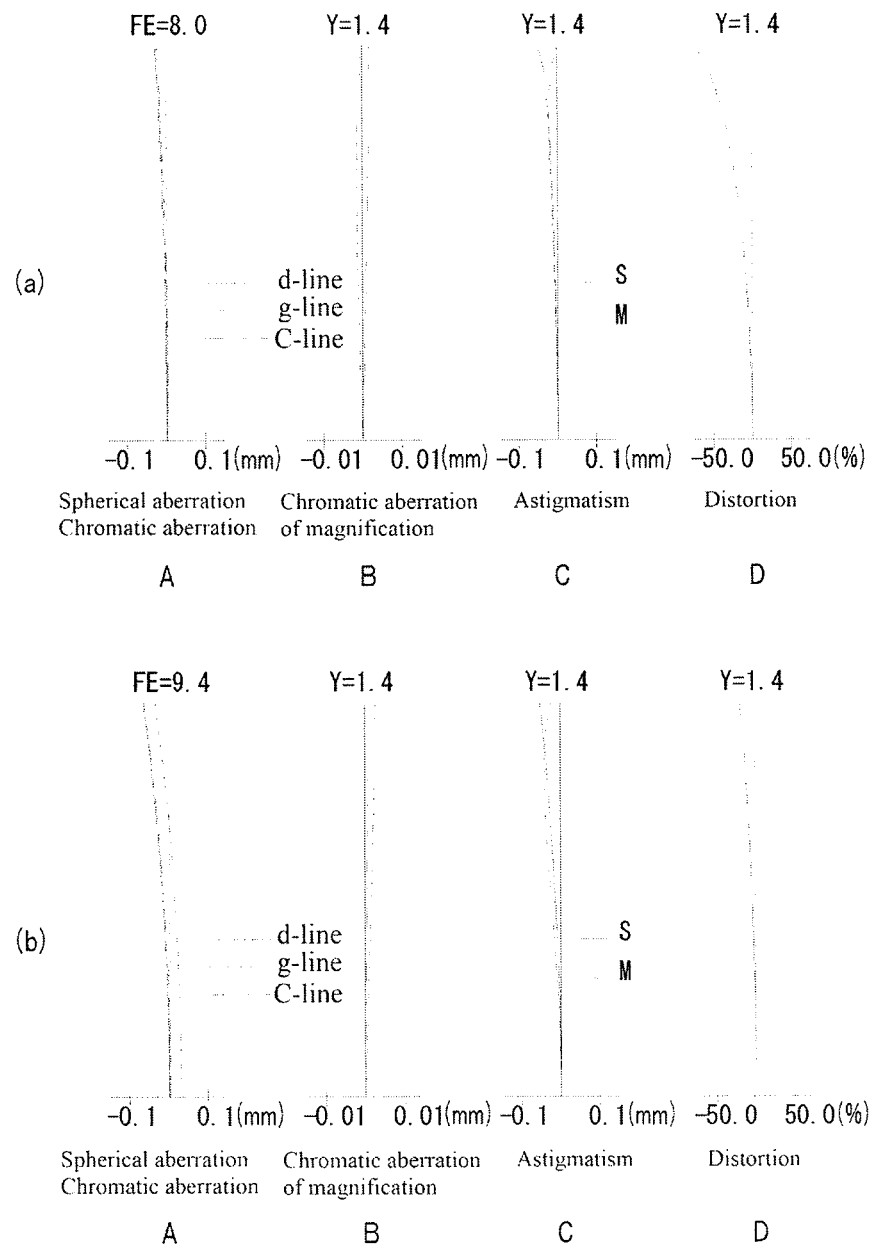
FIG. 15 is a diagram showing various aberrations in the endoscope magnification optical system according to Working Example 7 of the present invention.

As can be understood from FIGS. 14 and 15 and Table 7, although the endoscope magnification optical system 100 according to Working Example 7 is small, the optical performance (in particular, correction of astigmatism, comatic aberration, and chromatic aberration) is favorable at every magnification position from the wide angle end to the telephoto end.

Verification of Conditional Expressions

Table 8 is a list of values that are calculated when conditional expressions (1) to (4) are applied in Working Examples 1 to 7.

TABLE 8

| Conditional expression | Working Ex. 1 | Working Ex. 2 | Working Ex. 3 | Working Ex. 4 | Working Ex. 5 | Working Ex. 6 | Working Ex. 7 |
|---|---|---|---|---|---|---|---|
| (1) $m_{2w}$ | −0.641 | −0.607 | −0.493 | −0.535 | −0.526 | −0.467 | −0.52 |
| (1) $m_{2t}$ | −0.975 | −0.984 | −0.941 | −0.904 | −0.982 | −0.954 | −0.988 |
| (2) | 0.33 | 0.38 | 0.45 | 0.37 | 0.46 | 0.49 | 0.47 |
| (3) | 2.3 | 2.2 | 3.4 | 2.6 | 5.3 | — | — |
| (4) | — | — | — | — | — | 0.41 | 0.33 |

Also, as shown in Table 8, the endoscope magnification optical systems 100 according to Working Examples 1 to 5 satisfy conditional expressions (1) to (3). Also, as shown in Table 8, the endoscope magnification optical systems 100 according to Working Examples 6 and 7 satisfy conditional expressions (1), (2), and (4). With Working Examples 1 to 7, effects achieved due to the conditional expressions being satisfied are exhibited.

Exemplary embodiments of the present invention have been described above. The embodiments of the present invention are not limited to the content described above, and can be modified in various ways within the scope of the technical idea of the present invention. For example, content obtained by combining the embodiments and the like disclosed as examples in the specification or obvious embodiments and the like as appropriate is also included in the embodiments of the present application.

The invention claimed is:

1. An endoscope magnification optical system comprising, in order starting from an object side, a first lens group having negative power, a second lens group having positive power, and a third lens group including at least a meniscus lens with a concave surface facing the object side and a positive lens,
    the endoscope magnification optical system being configured to magnify an optical image by moving at least the second lens group in a direction of an optical axis of the optical system with respect to the first lens group, which is a fixed lens group, while a distance from a lens surface located the closest to the object of the first lens group to an image plane is kept constant.

2. The endoscope magnification optical system according to claim 1, wherein,
    in a case where a magnification of the second lens group at a telephoto end is defined as m2t, a magnification of the second lens group at a wide angle end is defined as m2w, a movement amount of the second lens group that is needed to change from the telephoto end to the wide angle end or from the wide angle end to the telephoto end is defined as d (unit: mm), and a focal length of the second lens group is defined as f2 (unit: mm), the following two conditional expressions:

$1 < m2t < m2w < −0.35$ and $0.3 < d/f2 < 0.6$ are satisfied.

3. The endoscope magnification optical system according to claim 1, wherein
    the first lens group includes at least one single lens and one doublet.

4. The endoscope magnification optical system according to claim 3, wherein
    the first lens group includes at least a negative lens and a doublet, or a doublet having negative power and a meniscus lens with a concave surface facing the object side.

5. The endoscope magnification optical system according to claim 1, wherein:
    the second lens group is composed of, in order starting from the object side, a positive lens and a doublet having positive power; and
    in a case where a focal length of the positive lens in the second lens group is defined as f21 (unit: mm) and a composite focal length from the first to third lens groups at a wide angle end is defined as fw (unit: mm), the following conditional expression:

$2 < f21/fw < 6$ is satisfied.

6. The endoscope magnification optical system according to claim 1, wherein
    the second lens group is composed of, in order starting from the object side, a positive lens, a positive lens, and a doublet having positive power.

7. The endoscope magnification optical system according to claim 6, wherein:

the two positive lenses included in the second lens group have mutually different focal lengths, and in a case where a composite focal length of the two positive lenses is defined as fc (unit: mm) and a longer focal length of the focal lengths of the two positive lenses is defined as fp (unit: mm), the following conditional expression:

$$0.3 < fc/fp$$

is satisfied.

8. The endoscope magnification optical system according to claim 1, wherein an aperture configured to move integrally with the second lens group on the optical axis is included between the first and the second lens groups.

9. An endoscope, wherein the endoscope magnification optical system according to claim 1 is mounted on a leading end of the endoscope.

* * * * *